United States Patent
de Juan et al.

(10) Patent No.: US 12,270,978 B2
(45) Date of Patent: Apr. 8, 2025

(54) DEVICES, SYSTEMS, AND METHODS FOR OTOLOGY

(71) Applicant: Spiral Therapeutics Inc., Brisbane, CA (US)

(72) Inventors: Eugene de Juan, Brisbane, CA (US); Signe Erickson, Brisbane, CA (US); Charles Limb, Brisbane, CA (US); Vrad Levering, Brisbane, CA (US)

(73) Assignee: Spiral Therapeutics Inc., Brisbane, CA (US)

( * ) Notice: Subject to any disclaimer, the term of this patent is extended or adjusted under 35 U.S.C. 154(b) by 1081 days.

(21) Appl. No.: 17/155,575

(22) Filed: Jan. 22, 2021

(65) Prior Publication Data

US 2021/0228411 A1    Jul. 29, 2021

Related U.S. Application Data

(60) Provisional application No. 63/082,996, filed on Sep. 24, 2020, provisional application No. 63/081,015, (Continued)

(51) Int. Cl.
*A61F 11/00* (2022.01)
*A61B 1/018* (2006.01)
(Continued)

(52) U.S. Cl.
CPC .......... *G02B 21/0012* (2013.01); *A61B 1/018* (2013.01); *A61B 1/227* (2013.01); (Continued)

(58) Field of Classification Search
CPC ............ G02B 21/0012; G02B 21/0032; G02B 21/22; G02B 23/2476; A61B 1/018; (Continued)

(56) References Cited

U.S. PATENT DOCUMENTS

| | | | |
|---|---|---|---|
| 5,421,818 A | 6/1995 | Arenberg | |
| 6,024,726 A | 2/2000 | Hill | |

(Continued)

FOREIGN PATENT DOCUMENTS

| | | |
|---|---|---|
| JP | 2002-536114 | 10/2002 |
| JP | 2019-522539 | 8/2019 |

(Continued)

OTHER PUBLICATIONS

Extended European Search Report in European Appln No. 21745163. 2, dated Jan. 26, 2024, 6 pages.
(Continued)

*Primary Examiner* — Michael J Tsai
*Assistant Examiner* — Justin L Zamory
(74) *Attorney, Agent, or Firm* — Fish & Richardson P.C.

(57) ABSTRACT

Systems and methods can be employed for facilitating access and procedures in the outer, middle, and inner ear in order to diagnose or treat ear disorders including, but not limited to hearing loss and excessive ear wax. In some examples, the systems and methods include instruments and techniques that facilitate trans-tympanic membrane or trans-fibrous ring access to the middle ear. The systems and methods can also be used to improve accessibility for various otological surgical procedures, such as, but not limited to, cholesteatoma removal, tympanic membrane repair and ossicular chain repair.

17 Claims, 17 Drawing Sheets

Related U.S. Application Data filed on Sep. 21, 2020, provisional application No. 63/080,510, filed on Sep. 18, 2020, provisional application No. 63/078,141, filed on Sep. 14, 2020, provisional application No. 63/077,448, filed on Sep. 11, 2020, provisional application No. 63/051,568, filed on Jul. 14, 2020, provisional application No. 63/040,495, filed on Jun. 17, 2020, provisional application No. 63/024,183, filed on May 13, 2020, provisional application No. 62/965,481, filed on Jan. 24, 2020.

(51) Int. Cl.

| | | |
|---|---|---|
| *A61B 1/227* | (2006.01) | |
| *A61B 17/29* | (2006.01) | |
| *A61B 17/32* | (2006.01) | |
| *A61B 17/3205* | (2006.01) | |
| *A61B 17/34* | (2006.01) | |
| *A61B 18/04* | (2006.01) | |
| *A61B 18/14* | (2006.01) | |
| *A61B 18/20* | (2006.01) | |
| *A61F 2/958* | (2013.01) | |
| *A61F 11/20* | (2022.01) | |
| *A61M 31/00* | (2006.01) | |
| *A61M 37/00* | (2006.01) | |
| *G02B 21/00* | (2006.01) | |
| *G02B 21/22* | (2006.01) | |
| *A61B 17/00* | (2006.01) | |
| *A61B 18/00* | (2006.01) | |
| *A61F 2/18* | (2006.01) | |

(52) U.S. Cl.
CPC ...... *A61B 17/29* (2013.01); *A61B 17/320068* (2013.01); *A61B 17/3205* (2013.01); *A61B 17/3423* (2013.01); *A61B 17/3468* (2013.01); *A61B 17/3478* (2013.01); *A61B 18/04* (2013.01); *A61B 18/1485* (2013.01); *A61B 18/20* (2013.01); *A61F 2/958* (2013.01); *A61F 11/20* (2022.01); *A61F 11/202* (2022.01); *A61M 31/00* (2013.01); *A61M 31/002* (2013.01); *A61M 37/0015* (2013.01); *G02B 21/0032* (2013.01); *G02B 21/22* (2013.01); *A61B 2017/00115* (2013.01); *A61B 2017/00787* (2013.01); *A61B 2017/00867* (2013.01); *A61B 2017/32007* (2017.08); *A61B 2018/00327* (2013.01); *A61B 2217/005* (2013.01); *A61F 2002/183* (2013.01); *A61F 2250/0067* (2013.01); *A61M 2037/0023* (2013.01); *A61M 2037/0046* (2013.01); *A61M 2205/04* (2013.01); *A61M 2210/0662* (2013.01); *A61M 2210/0668* (2013.01)

(58) Field of Classification Search
CPC . A61B 1/227; A61B 17/29; A61B 17/320068; A61B 17/3205; A61B 17/3423; A61B 17/3468; A61B 17/3478; A61B 18/04; A61B 18/1485; A61B 18/20; A61B 2017/00115; A61B 2017/00787; A61B 2017/00867; A61B 2017/32007; A61B 2018/00327; A61B 2217/005; A61B 2017/00544; A61B 2017/00738; A61B 2017/00907; A61B 2017/305; A61B 17/205; A61B 2017/320028; A61B 17/32002; A61B 17/3201; A61B 2017/320069; A61B 2017/3445; A61B 2017/3447; A61B 17/22012; A61B 2017/00323; A61B 2017/00331; A61B 2017/345; A61F 2/958; A61F 11/20; A61F 11/202; A61F 2002/183; A61F 2250/0067; A61F 11/00; A61M 31/00; A61M 31/002; A61M 37/0015; A61M 2037/0023; A61M 2037/0046; A61M 2205/04; A61M 2210/0662; A61M 2210/0668

See application file for complete search history.

(56) References Cited

U.S. PATENT DOCUMENTS

| | | |
|---|---|---|
| 6,045,528 A | 4/2000 | Arenberg et al. |
| 6,120,484 A | 9/2000 | Silverstein |
| 6,277,148 B1 * | 8/2001 | Dormer ............... H04R 25/606 623/10 |
| 6,440,102 B1 | 8/2002 | Arenberg et al. |
| 6,648,873 B2 | 11/2003 | Arenberg et al. |
| 7,351,246 B2 | 4/2008 | Epley |
| 7,704,259 B2 | 4/2010 | Kaplan et al. |
| 8,197,461 B1 | 6/2012 | Arenberg et al. |
| 9,352,084 B2 | 5/2016 | Decker et al. |
| 9,616,207 B2 | 4/2017 | Verhoeven et al. |
| 10,130,514 B2 | 11/2018 | Imran et al. |
| 10,492,670 B1 | 12/2019 | Bendory et al. |
| 2003/0220536 A1 | 11/2003 | Hissong |
| 2004/0133099 A1 | 7/2004 | Dyer et al. |
| 2004/0172005 A1 | 9/2004 | Arenberg et al. |
| 2004/0181185 A1 | 9/2004 | Lee |
| 2006/0184143 A1 * | 8/2006 | Jolly ....................... A61F 11/00 604/151 |
| 2011/0224629 A1 | 9/2011 | Jolly et al. |
| 2012/0179187 A1 | 7/2012 | Loushin et al. |
| 2012/0203200 A1 | 8/2012 | Kenney et al. |
| 2013/0060131 A1 | 3/2013 | Oghalai et al. |
| 2013/0085476 A1 | 4/2013 | Imran |
| 2013/0245569 A1 | 9/2013 | Jolly et al. |
| 2016/0346511 A1 | 12/2016 | Cohen et al. |
| 2017/0172804 A1 | 6/2017 | Watanabe et al. |
| 2017/0354431 A1 | 12/2017 | Rubin et al. |
| 2018/0303314 A1 | 10/2018 | Noyes |
| 2019/0015254 A1 | 1/2019 | Bendory et al. |
| 2019/0321610 A1 | 10/2019 | Goldfarb et al. |
| 2019/0350607 A1 | 11/2019 | Martone et al. |
| 2020/0094030 A1 | 3/2020 | Kim et al. |

FOREIGN PATENT DOCUMENTS

| | | |
|---|---|---|
| WO | WO 2008097317 | 8/2008 |
| WO | WO 2019152866 | 8/2019 |
| WO | WO 2019200259 | 10/2019 |
| WO | WO 2020115674 | 6/2020 |

OTHER PUBLICATIONS

International Preliminary Report on Patentability in International Appln. No. PCT/US2021/014601, mailed on Aug. 4, 2022, 9 pages.
PCT Invitation to Pay Additional Fees and, where Applicable, Protest Fee in International Appln. No. PCT/US2021/14601, dated Mar. 30, 2021, 2 pages.
PCT International Search Report and Written Opinion in International Appln. No. PCT/US2021/014601, dated Jun. 3, 2021, 12 pages.

* cited by examiner

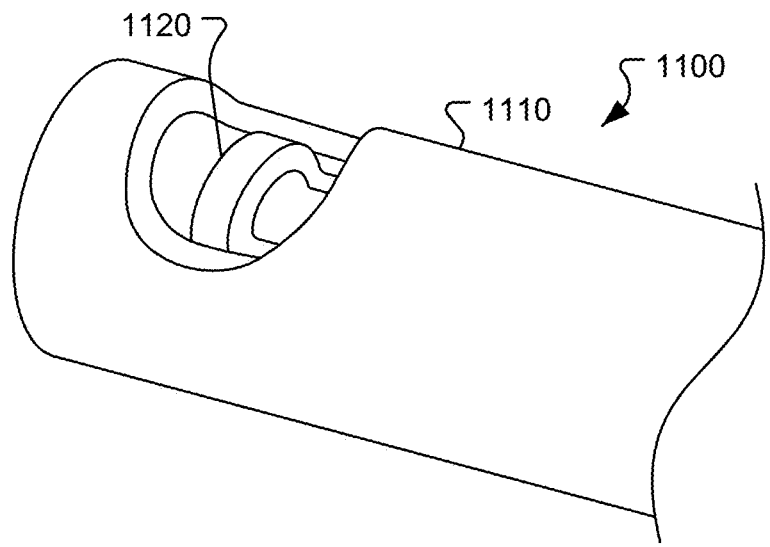
FIG. 23
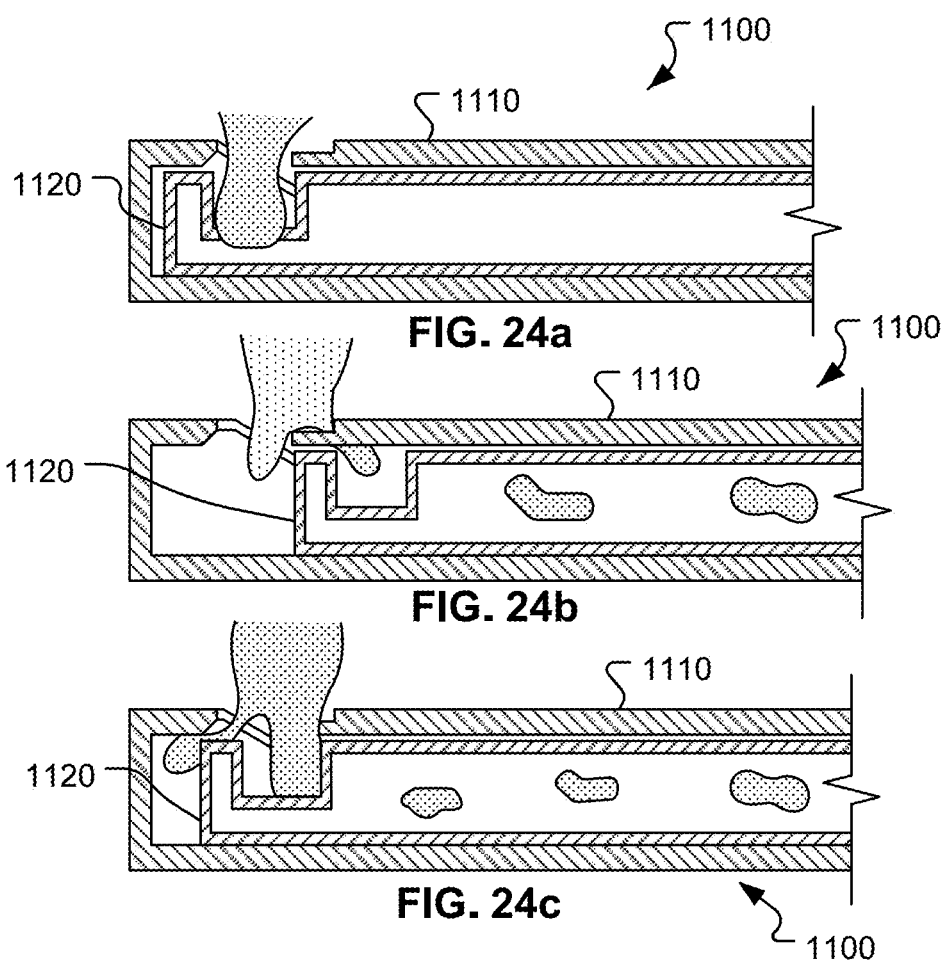
FIG. 24a
FIG. 24b
FIG. 24c

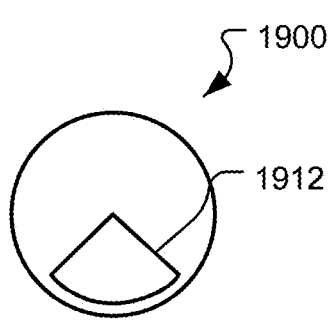
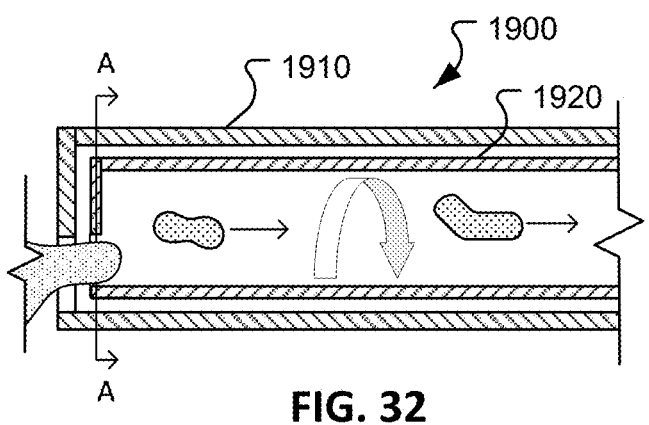
FIG. 33
FIG. 32
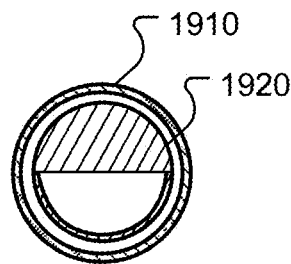
CROSS-SECTIONAL VIEW A--A
FIG. 34A
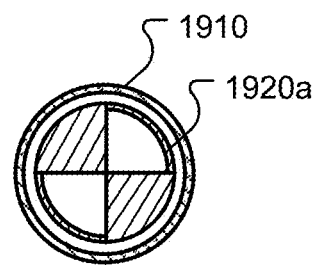
ALTERNATIVE CROSS-SECTIONAL VIEW A--A
FIG. 34B

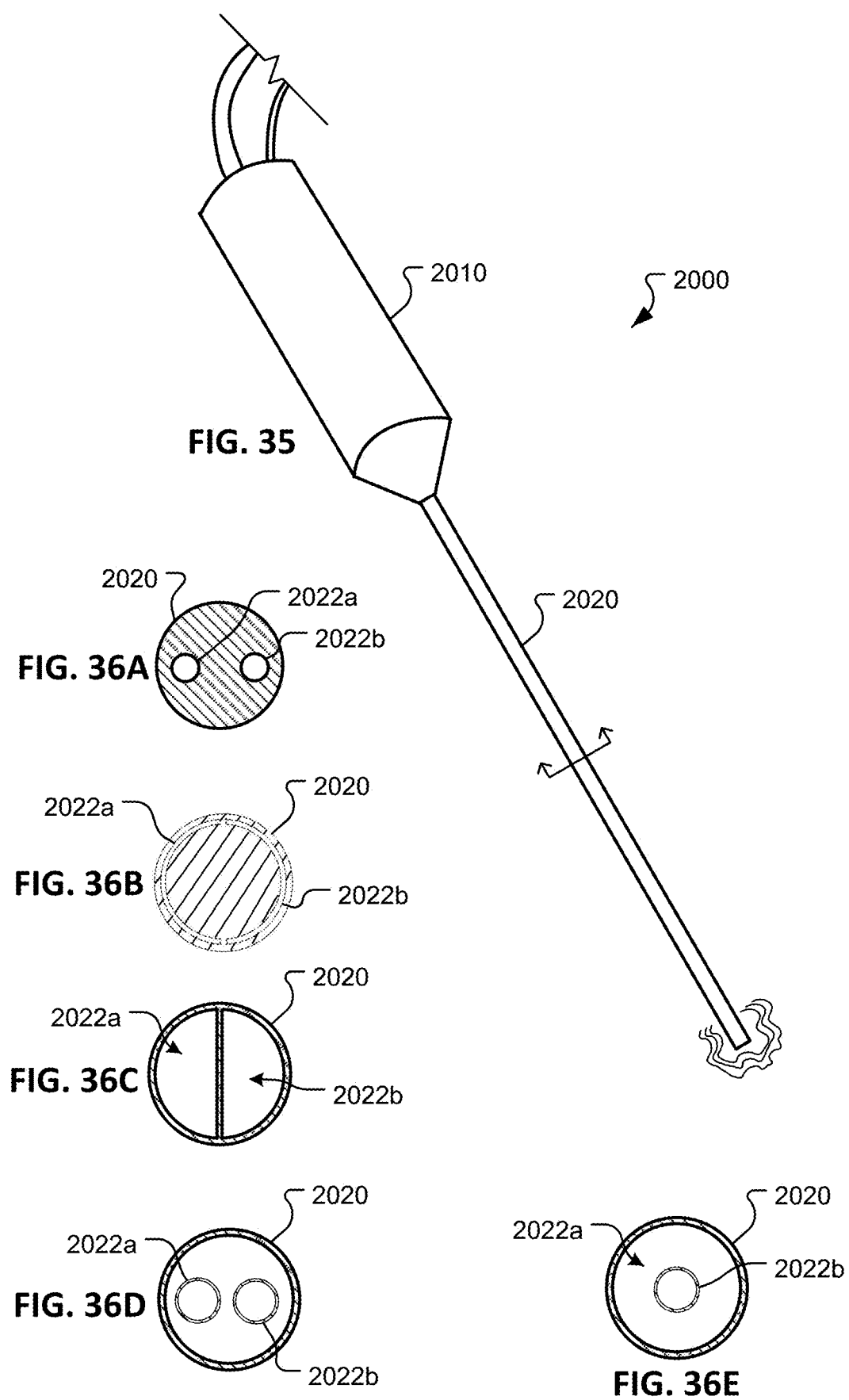

DEVICES, SYSTEMS, AND METHODS FOR OTOLOGY

CROSS-REFERENCE TO RELATED APPLICATIONS

This application claims the benefit of priority to U.S. Provisional Application No. 62/965,481 filed on Jan. 24, 2020, U.S. Provisional Application No. 63/024,183 filed on May 13, 2020 (which is fully incorporated herein by reference), U.S. Provisional Application No. 63/040,495 filed on Jun. 17, 2020 (which is fully incorporated herein by reference), U.S. Provisional Application No. 63/051,568 filed on Jul. 14, 2020 (which is fully incorporated herein by reference), U.S. Provisional Application No. 63/077,448 filed on Sep. 11, 2020 (which is fully incorporated herein by reference), U.S. Provisional Application No. 63/078,141 filed on Sep. 14, 2020 (which is fully incorporated herein by reference), U.S. Provisional Application No. 63/080,510 filed on Sep. 18, 2020 (which is fully incorporated herein by reference), U.S. Provisional Application No. 63/081,015 filed on Sep. 21, 2020 (which is fully incorporated herein by reference), and U.S. Provisional Application No. 63/082,996 filed on Sep. 24, 2020 (which is fully incorporated herein by reference).

TECHNICAL FIELD

This document relates to systems, methods, and materials for facilitating access and procedures in the outer, middle, and inner ear in order to diagnose or treat disorders including, but not limited to hearing loss, excessive earwax buildup, and other ear disorders. In some examples, the systems and methods include instruments and techniques that facilitate trans-tympanic membrane or trans-fibrous ring access to the middle ear.

BACKGROUND

The human ear is subject to a variety of disorders including, but not limited to, excessive earwax buildup, hearing loss, tinnitus, balance disorders including vertigo, Meniere's disease, vestibular neuronitis, vestibular schwannoma, labyrinthitis, otosclerosis, ossicular chain dislocation, cholesteatoma, outer ear infections, middle ear infections, schwannoma, and tympanic membrane perforations, to provide a few examples.

Access through the ear canal to the tympanic membrane, middle ear, and inner ear has historically been challenging due to angulation of the ear canal, sensitivity of the ear canal walls, the small cumulative cross-section of the ear canal taking into account the angulation of the canal, large size of the shafts and functional tips of the available instruments, structures creating corners and blocked spaces in the middle ear, and lack of methods or systems for enabling access to the middle or inner ear. Moreover, instruments specifically designed for various otologic procedures are lacking.

SUMMARY

This document describes systems and methods for otologic procedures such as, but not limited to, removal of excessive earwax buildup in the outer ear. This document also describes systems and methods for minimally invasive access to the middle ear for purposes of delivering surgical or medical treatment for inner and middle ear disorders.

For example, this document describes systems and methods for trans-tympanic membrane access and trans-fibrous ring access to achieve minimally invasive delivery of various treatments. The devices, systems, materials, compounds, compositions, articles, and methods described herein may be used to treat a variety of disorders of the middle ear and/or inner ear including, but not limited to, hearing loss, tinnitus, balance disorders including vertigo, Meniere's disease, vestibular neuronitis, vestibular schwannoma, labyrinthitis, otosclerosis, ossicular chain dislocation, cholesteatoma, outer ear infections, middle ear infections, schwannoma, and tympanic membrane perforations, to provide a few examples. In some embodiments, the treatments facilitated by the systems and methods described herein include the delivery of therapeutic formulations into the round window niche and adjacent to the round window membrane of the cochlea under direct visualization. In particular implementations, the active agent of the therapeutic formulation may then transfer passively by diffusion across the round window membrane(s), according to a concentration gradient, into the perilymph (within the cochlea). In some embodiments, devices and methods supporting intracochlear delivery of therapeutics or implants are also described herein.

In one aspect, this document is directed to a surgical instrument configured for otologic procedures. The instrument includes a handle defining a longitudinal handle axis, an actuation mechanism coupled to the handle, and an instrument shaft extending from the handle and defining a longitudinal shaft axis. The longitudinal shaft axis extends at a non-zero angle relative to the longitudinal handle axis.

Such a surgical instrument configured for otologic procedures can optionally include one or more features. In some embodiments, the instrument is an injection instrument configured to deliver a therapeutic formulation within the middle ear. The instrument can be an injection instrument configured to deliver a therapeutic formulation to a round window niche within the middle ear. The instrument can be instrument a forceps instrument, a diathermy instrument, an aspirating tissue cutter instrument, and/or an ultrasonic instrument.

In another aspect, this document is directed to another surgical instrument configured for otologic procedures. The instrument includes a handle, an actuation mechanism coupled to the handle, and an instrument shaft extending from the handle. The instrument shaft is curved.

In another aspect, this disclosure is directed to a method of treating a middle ear or inner ear disorder of a patient. The method includes accessing the middle ear of the patient by advancing a distal end portion of an otologic instrument through or adjacent to an annulus tympanicus of the patient.

Such a method of treating a middle ear or inner ear disorder of a patient may optionally include one or more of the following features. The method may also include implanting a port device in the annulus tympanicus. The advancing the distal end portion of the otologic instrument through or adjacent to the annulus tympanicus can be performed by passing the distal end portion of the otologic instrument through a passage defined by the port device. In some embodiments, the passage is curved and causes the distal end portion of the otologic instrument to curve as the distal end portion of the otologic instrument is passed through the passage. The method may also include making a puncture or incision in or adjacent to the annulus tympanicus. The advancing the distal end portion of the otologic instrument through or adjacent to the annulus tympanicus may be performed by passing the distal end portion of the otologic instrument through the puncture or incision. In some embodiments, the otologic instrument is a first otologic instrument, and the method may also include accessing the middle ear of the patient by advancing a distal end portion of a second otologic instrument through or adjacent to the annulus tympanicus of the patient. The distal end portions of the first and second otologic instruments may be in the middle ear concurrently. In some embodiments, the first otologic instrument is an endoscope and the second otologic instrument is an injection instrument configured to deliver a therapeutic formulation within the middle ear. In particular embodiments, the first otologic instrument is an endoscope and the second otologic instrument is a diathermy instrument or an ultrasonic instrument. In certain embodiments, the first otologic instrument is an endoscope and the second otologic instrument is an aspirating tissue cutter instrument. The method may also include flooding the middle ear with a liquid and, while the middle ear is flooded with the liquid, treating the middle ear or inner ear disorder using the otologic instrument.

In another aspect, this disclosure is directed to another method of treating an ear disorder of a patient. The method includes flooding a middle ear with a liquid. The method also includes treating the ear disorder using one or more otologic instruments while the middle ear is flooded with the liquid.

Such a method of treating the ear disorder of the patient may optionally include one or more of the following features. In some embodiments, the one or more otologic instruments includes an aspirating tissue cutter instrument, and the treating the ear disorder includes removing membranes or fibrous tissues in a middle ear using the aspirating tissue cutter instrument. In particular embodiments, the one or more otologic instruments includes an aspirating tissue cutter instrument, and the treating the ear disorder includes removing tissue along an edge of a tympanic membrane perforation.

Some or all of the embodiments described herein may provide one or more of the following advantages. First, the systems and methods for treating hearing loss, and all other ear disorders as described herein, can include specialized instruments and techniques that can be used to access outer ear, middle ear, and/or inner ear areas including, for example, the round window niche of the cochlea. New types of otology instruments are described herein, such as instruments for micro-diathermy, pneumatically driven cutters, suction cutters, micro-suction, ultrasonic cutters/debriders, and so on, and combinations thereof. The specialized instruments and techniques described herein facilitate the performance of new types of therapeutic treatments for inner and middle ear disorders. In addition, current therapeutic treatments can be performed with enhanced efficacy and efficiency using the specialized instruments and techniques described herein.

Second, the systems and methods for treating hearing loss and other ear disorders as described herein facilitate treatments in a minimally invasive fashion. Such minimally invasive techniques can tend to reduce recovery times, patient discomfort, and treatment costs. Moreover, the methods described herein can be performed using a local anesthetic rather than requiring general anesthesia. Accordingly, the treatment cost, patient risks, recovery times, and recurrence rates are further advantageously reduced.

Third, the systems and methods for treating hearing loss and other ear disorders as described herein allow direct access to the middle ear cavity through or adjacent to the tough fibrous ring (annulus tympanicus) surrounding the tympanic membrane in a suture-less, low impact manner. In some implementations, such trans-fibrous ring access through the annulus tympanicus can be safer (e.g., less risk of tearing or damaging the tympanic membrane mid-procedure), less invasive, and achieved with no sealing or patching after the procedure.

Fourth, console systems for otology procedures are described herein that advantageously consolidate and integrate multiple treatment modalities for enhanced synchronized functionality. The integration also provides convenience and efficiency improvements by eliminating the need for clinicians to move back and forth between the controls of separate systems throughout the treatment procedure, thus increasing surgical precision.

Fifth, methods are described herein for temporarily filling the middle ear and/or outer ear cavities such that treatment procedures can be performed "underwater." This approach confers a number of advantages such as, but not limited to, maintaining fluid equilibrium in the cochlea during surgery, tamponade bleeding, enabling aspiration procedures that allow for constant irrigation or washing of middle ear structures, improving visualization, and enabling the precise use of suction cutters to trim or remove tissues during surgery, and so on, as described herein.

Sixth, devices are described herein that can deliver ultrasonic energy to cause fragmentation, emulsification or resurfacing of materials such as, but not limited to, earwax, membranes, tumors, cholesteatoma, skin, bone, and the like. Some such ultrasonic devices are especially designed to be used in air, and therefore are cooled by internal fluid circulation, irrigation/aspiration, or other ways, as described herein.

Seventh, devices are described herein that combine illumination and/or aspiration with diathermy in a single instrument. Such a combination can advantageously provide a one-handed instrument with multiple useful functionalities.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 23 shows another example end effector that can be incorporated in the otology instruments described herein.

FIG. 24a-24c are a series of figures that illustrate how the end effector of FIG. 23 functions to cut and aspirate tissues.

FIG. 32 is a longitudinal cross-sectional view of another example end effector that can be incorporated in the otology instruments described herein.

FIG. 33 is an end view of the instrument of FIG. 32.

FIG. 34A is a transverse cross-sectional view of the instrument of FIG. 32.

FIG. 34B is an alternative cross-sectional view of the instrument of FIG. 32.

FIG. 35 shows another type of example instrument that can be incorporated as part of the otology instruments described herein.

FIGS. 36A-E show various examples of alternative transverse cross-sections of the shaft of the instrument of FIG. 35.

Like reference symbols in the various drawings indicate like elements.

DETAILED DESCRIPTION OF ILLUSTRATIVE EMBODIMENTS

Figure 1:
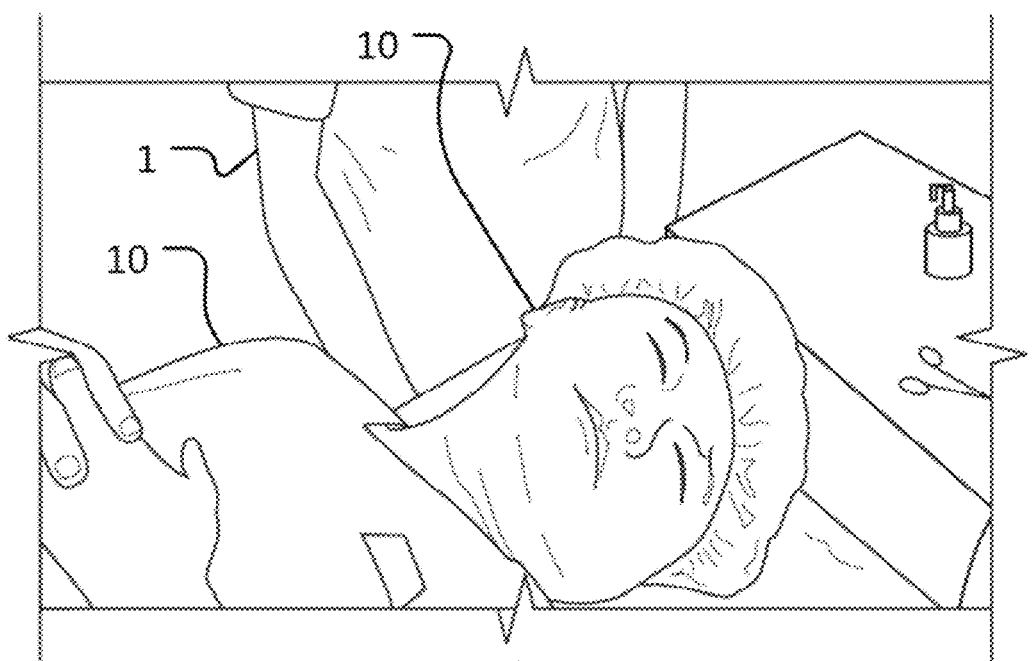
FIG. 1 shows a patient in position for a medical procedure for treating hearing loss and other ear disorders, in accordance with some embodiments described herein.

Referring to FIG. 1, in some cases a patient 10 can be oriented in an example suitable position as shown to receive various procedure(s) to treat ear disorders including, but not limited to, ear wax removal, sensorineural hearing loss (including hidden hearing loss, noise-induced hearing loss, age-related hearing loss, drug-induced hearing loss (e.g., chemotherapy-induced hearing loss or aminoglycoside-induced hearing loss), sudden sensorineural hearing loss (SNHL), autoimmune inner ear disease, and the like), tinnitus, balance disorders including vertigo, Meniere's disease, vestibular neuronitis, vestibular schwannoma, labyrinthitis, otosclerosis, ossicular chain dislocation, cholesteatoma, outer ear infections, middle ear infections, schwannoma, and tympanic membrane perforations.

In some cases, the procedures can be performed with the patient 10 fully supine (as shown) or reclined in a chair. The head of the patient 10 can, for example, be rotated to between about 30 to 45 degrees away from the clinician 1 (toward the opposite ear of the patient 10). The jaw of the patient 10 can be slightly elevated, and/or the external portion of the ear of the patient 10 may be pulled superiorly and backward to adjust the canal aperture and angularity. As such, the round window of the inner ear of the patient 10 will be oriented generally upward (e.g., away from the ground).

In some implementations, the patient 10 remains awake during the procedure(s) to treat ear disorders. That is, procedures can be performed using a local anesthetic rather than a general anesthetic. For example, in some cases agents such as phenol or lidocaine can be applied to the tympanic membrane ("TM") as a local anesthetic to facilitate the procedure. In some cases, the patient 10 can be given general anesthesia for the procedure.

This disclosure describes treatment methods and devices for treating the patient 10 using a minimally invasive approach. As described further below, particular embodiments of systems and methods for treating the patient 10 can include an improved set of otology medical instruments and improved treatment techniques.

Figure 2:
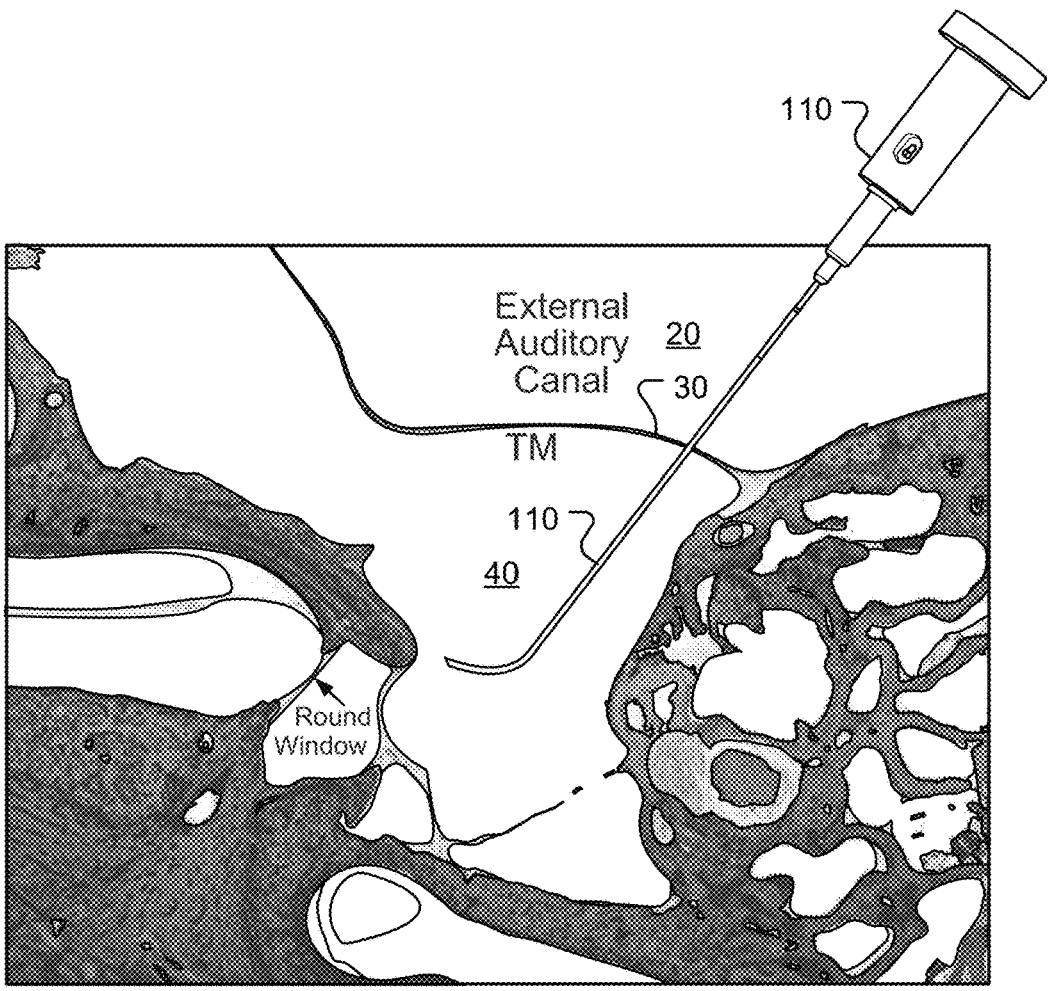
FIG. 2 illustrates an instrument being used to gain minimally invasive access to the middle ear through the tympanic membrane in accordance with some embodiments.

Referring also to FIG. 2, after prepping the patient 10 for the procedure, the clinician 1 treats the patient 10 using various otology instruments as described further below (at least one of which being represented in FIG. 2 by a generic instrument 110). For example, as depicted here, the instrument 110 can be advanced into the outer ear canal 20 toward the TM 30, and then advanced through the TM 30 such that a distal end portion of the instrument 110 is in the middle ear 40. In some cases, an endoscope (not shown) is used in the outer ear canal 20 to provide direct visualization as the instrument 110 is advanced. In some cases, a microscope or other magnifying instrument is used to provide direct visualization as the instrument 110 is advanced.

While a single instrument 110 is depicted in FIG. 2, in some cases two or more instruments 110 are concurrently used within the middle ear 40. For example in some embodiments a first instrument 110 may be an endoscope and a second instrument 110 may include an end effector for grasping, cutting, tearing, cauterizing, injecting, aspirating, irrigating, and so on, and combinations thereof. The endoscope can be used to provide visualization within the middle ear 40 while the second instrument 110 is being used to provide treatment.

The depicted example approach to the middle ear 40 is trans-tympanic membrane. That is, the instrument is passing through the TM 30. In some cases, the instruments 110 are advanced through the TM 30 via one or more temporarily implanted tympanic membrane port devices, such as those described in U.S. Patent Application 63/024,183 filed on May 13, 2020, which is incorporated herein by reference for all purposes. In some cases, the instrument 110 is advanced directly through an opening made in the TM 30 (e.g., via an incision or puncture made to the TM 30, without a tympanic membrane port device within the opening of the TM 30).

Figures 3, 4:
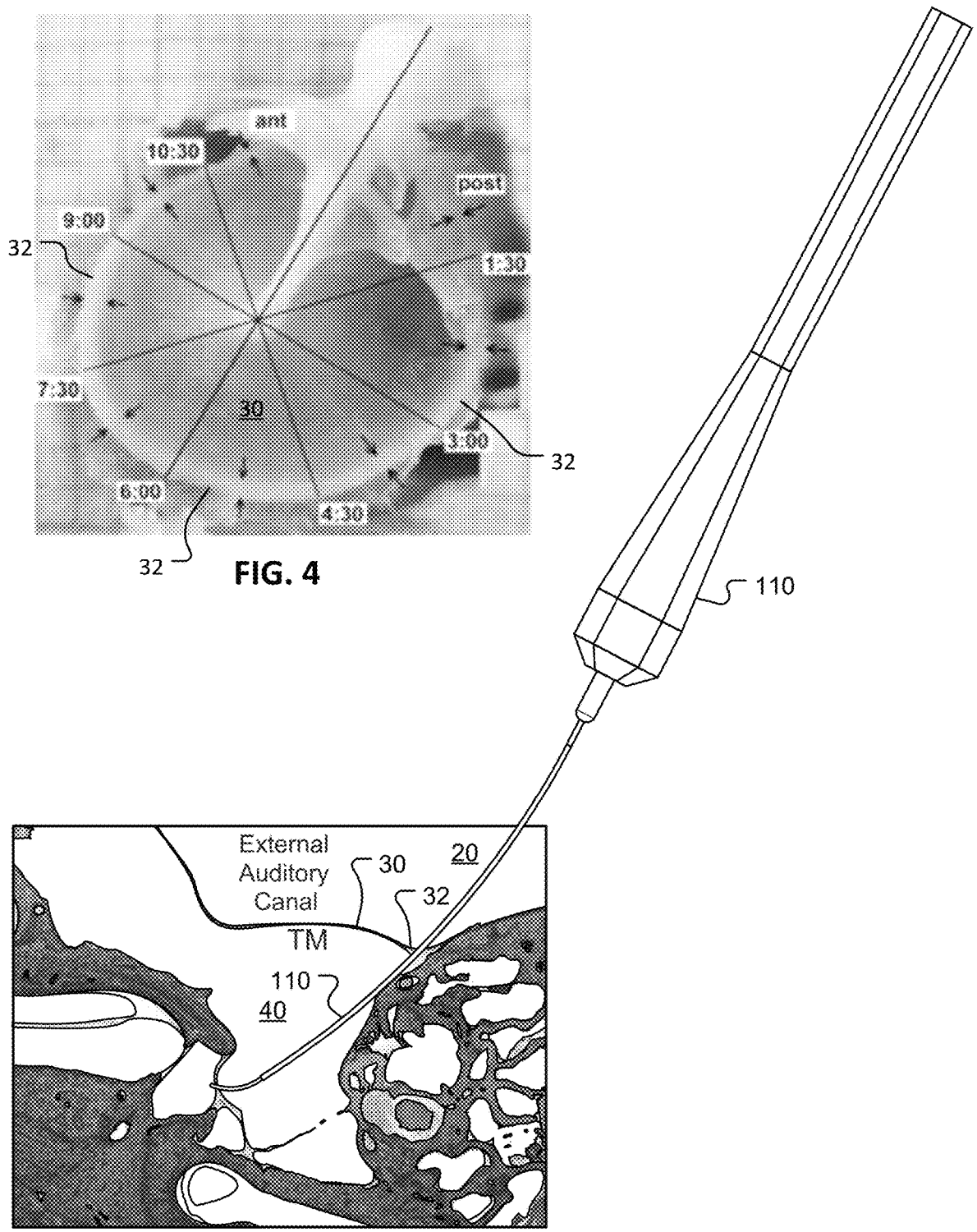
FIG. 3 illustrates an instrument being used to gain minimally invasive access to the middle ear through the annulus tympanicus (tough fibrous ring surrounding the tympanic membrane) in accordance with some embodiments.
FIG. 4 illustrates a right tympanic membrane with overlaid lines and markings that indicate coordinates of locations around the annulus tympanicus surrounding the tympanic membrane.

Referring to FIG. 3, in addition to, or as an alternative to, the trans-tympanic membrane approach to access the middle ear 40 as described above, in some cases the middle ear 40 can be accessed by passing through the annulus tympanicus 32 (the tough fibrous ring surrounding the TM 30). This approach can also be referred to as a trans-fibrous ring access or trans-annulus access to the middle ear 40. In such a case, the distal end portions of one or more instruments 110 can be passed through the annulus tympanicus 32 using a port device, or through a puncture/incision in the annulus tympanicus 32 without a port device.

Although access to the middle ear 40 through the TM 30 (the trans-tympanic membrane approach) is a viable technique, because of the fragility of the TM 30 care must be taken to prevent damage to the TM 30. The TM 30 however has a tough fibrous ring, the annulus tympanicus 32, extending around the periphery or circumference of the TM 30. As an example, the anterior portion of the annulus tympanicus 32 (the most directly accessible section via the ear canal 20) is covered by a thin layer of skin and lies on top of bone. In some embodiments, access to the middle ear 40 can be attained by passing through, or adjacent to, the annulus tympanicus 32, e.g., using sub-annular, trans-annular, or peri-annular approaches. This approach would be advantageous to mitigate concerns about tearing or damaging the TM 30 mid-procedure.

While a single instrument 110 is depicted in FIG. 3, in some cases two or more instruments 110 are concurrently used within the middle ear 40 using the depicted trans-annulus access. For example in some embodiments a first instrument 110 may be an endoscope and a second instrument 110 may include an end effector for grasping, cutting, cauterizing, injecting, aspirating, viewing, irrigating, and so on, and combinations thereof. The endoscope can be used to provide visualization within the middle ear 40 while the second instrument 110 is being used to provide treatment.

The annulus tympanicus 32 does tend, in some cases, to lie near the chorda tympani and/or facial nerves, and in some embodiments an access port device or other aid can be temporarily anchored through the annulus tympanicus 32 for subsequent insertion of the instrument therethrough while reducing blood loss, total tissue damage, and preventing accidental puncture or damage of nearby nerves.

Referring also to FIG. 4, a TM 30 is shown with its peripheral annulus tympanicus 32. Locations on the annulus tympanicus 32 can be identified using a clock face analogy with the malleus located at 12 o'clock, as shown. Some beneficial locations for passing through the annulus tympanicus 32 with instruments 110 would be between the 3-5 o'clock positions for the left ear (best 4-5), and between the 7-9 o'clock positions for the right ear (7-8 best). Additional beneficial locations for passing through the annulus tympanicus 32 with instruments 110 would be between the 4-5 o'clock positions for the left ear, and between the 7-8 o'clock positions for the right ear.

In some embodiments, one or more port devices having a throughway passage to facilitate sliding instrument access could be temporarily implanted in the annulus tympanicus 32. In some embodiments, the passage defined by the port device would have a curve or angulation to it. Such a curve or angulation could be advantageous for use with externally-deflectable instruments 110. Such instruments 110 could have one or more sections, such as a spiral-cut portion or otherwise flexible portion, that allows deflection of the tip or shaft of the instrument 110 such that as the instrument 110 passes through the curved passage defined by the port device the instrument 110 is redirected accordingly. As described herein, this can be advantageous for redirecting the instrument 110 more towards the central portion of the middle ear 40 or other desired target area without requiring actuation of the instrument 110.

In some embodiments, the various procedure(s) to treat ear disorders as described herein can be partially or entirely performed while a liquid is filling the middle ear 40 and or the outer ear 20. The cavity of the middle ear 40 is normally filled with air. A liquid (e.g., saline, water, etc.) could be used to temporarily fill the cavity of the middle ear 40 such that treatment procedures described herein could be performed "underwater." This approach would confer a number of advantages.

When placing cochlear implant electrodes, the fluid compartment of the cochlea is breached. This can result in loss of perilymph fluid, which gushes or oozes into the air-filled middle ear 40, leading to dizziness and/or irreversible damage of the delicate cellular structures of the cochlea. Filling the cavity of the middle ear 40 with an artificial perilymph-like fluid (e.g., artificial cerebrospinal fluid with higher protein concentration) could maintain fluid equilibrium in the cochlea during surgery.

When performing middle ear or inner ear surgery (e.g., cholesteatoma surgery or stapedectomy), the round window membrane or the oval window can be disrupted, resulting in loss of perilymph fluid, which gushes or oozes into the air-filled middle ear 40, leading to dizziness and irreversible damage of the delicate cellular structures of the cochlea. Filling the cavity of the middle ear 40 with an artificial perilymph-like fluid (e.g. artificial cerebrospinal fluid with higher protein concentration) could maintain fluid equilibrium in the cochlea during surgery.

Intraoperative hemorrhage in the middle ear space 40 must be constantly managed during surgical procedures. Maintaining a liquid filled compartment in the middle ear 40 could help to tamponade bleeding, particularly if a heavy liquid such as a sodium hyaluronate-based viscoelastic (e.g., Healon, DuoVisc, ProVisc or Viscoat) or silicone oil is used.

Maintaining a constant infusion of simple saline solution or artificial perilymph-like fluid in the middle ear 40 could allow for aspiration procedures to be performed which would allow for constant irrigation or washing of ear structures. This could be beneficial in controlling bleeding and in allowing for the use of aspirating ultrasonic instruments for tissue removal and aspirating pneumatic cutters. These instruments could simultaneously provide infusion and aspiration. Alternatively, a central console, as described further below, could control an infusion line into the ear and aspiration of individual instruments to maintain constant fluid volume and pressure. In either case, simultaneous infusion and aspiration would minimize the need for frequent instrument exchanges and allow for more efficient removal of blood and other debris.

An endoscope could be used to enable visualization of the liquid-filled ear 40. Using an endoscope in a liquid-filled space removes concerns or difficulties with fogging or blood obscuring the lens, and the associated subsequent need to clean the lens of the endoscope. Alternatively, a lens could be placed at the air/liquid interface to allow for visualization through the microscope (similar to a swimmer's mask). The lens could have ports through or around it to allow for instrument passage. In some embodiments, such a lens can be made to provide a wide viewing angle.

In the case of tympanoplasty, it may be advantageous to fill all or a portion of the ear canal with fluid, in addition to the middle ear cavity. This would provide additional mechanical support to the tympanic membrane and allow for an aspirating cutter to be used for trimming the edges of the perforation.

Figure 5:
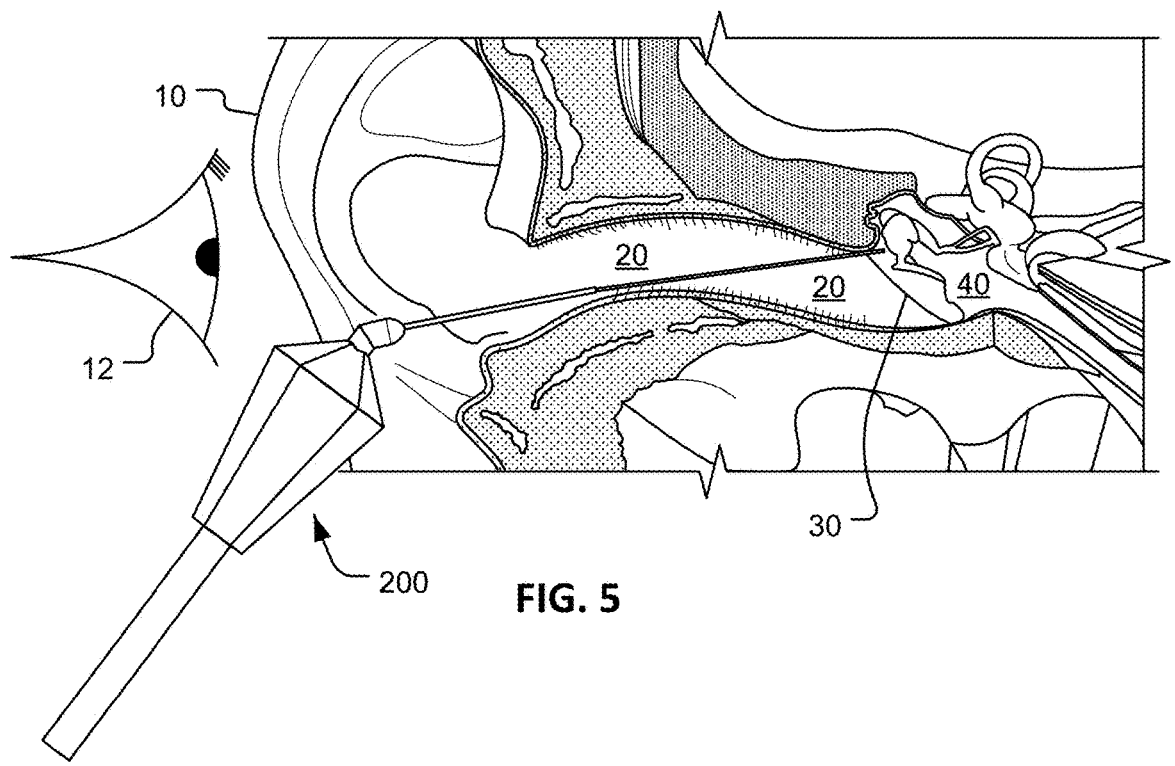
FIG. 5 schematically illustrates an example of how an instrument can be designed to allow for visualization within the outer ear canal while the instrument is in use.

Referring to FIG. 5, an instrument 200 is shown extending into the outer ear 20 of the patient 10 toward the TM 30. A symbol of an eye 12 is also shown as a representation of the need of the clinician 1 to use an endoscope, a microscope, or other optical instrument to obtain direct visualization within the outer ear 20 as the instrument 200 is advanced. Because the canal of the outer ear 20 is relatively small in cross-section, and may be curved or angulated, the actual room for the instrument 200 and the visualization device is quite limited. As described further below, the instruments described herein are designed to mitigate some of the competing needs for space between the instruments 200 and the visualization device used by the clinician 1. In addition, the instruments described herein are designed to facilitate the use of two or more instruments 200 concurrently.

Current instruments used for otologic procedures are typically largely unchanged in design or use from many years ago. Although there have been some advancements in endoscopes used in otologic procedures, such endoscopes still have relatively large diameter shafts (e.g., approximately 2 mm) that are straight and stiff. Even ear canal-based approaches still use instruments that have relatively large diameter shafts (e.g., 1.5 mm to 7 mm) and straight handles. For the few otologic instruments that are actuable (e.g., scissors) the actuation requires large hand and finger movements that interfere with holding the functional distal tip in position. Additionally, such handles frequently obstruct the microscope view.

Variable anatomical widths and curvatures of ear canals 20 (from patient to patient) also limit the possible instrument ranges of motion, and can limit simultaneous use of more than one instrument without the handles or shafts of the instruments interfering with each other. Additionally, once the TM 30 is reached down the ear canal 20, the TM 30 is oblique to the direction of view, thereby increasing the difficulty of interacting through the TM 30.

Figure 6:
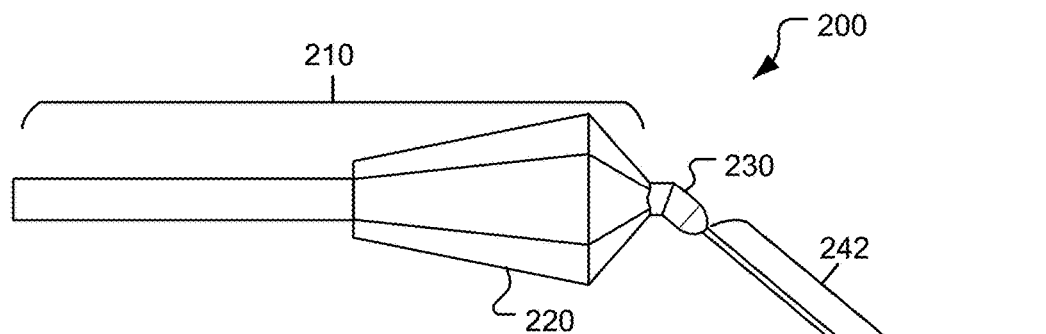
FIG. 6 shows an example otology instrument in accordance with some embodiments.

Referring to FIG. 6, an example otologic instrument 200 is angulated to facilitate its use, as described further below, in a manner that facilitates direct visualization and/or the use of two otologic instruments 200 concurrently. The otologic instrument 200 includes a handle 210, an actuation mechanism 220, an angulation portion 230, and an instrument shaft 240. The actuation mechanism 220 is coupled to the handle 210, or comprises a portion of the handle 210. The angulation portion 230 is coupled to and distally extends from the handle 210 and/or the actuation mechanism 220. The instrument shaft 240 is coupled to and distally extends from the angulation portion 230. The otologic instrument 200 can be reusable or disposable.

In the depicted embodiment, the instrument shaft 240 includes a proximal portion 242, a distal end portion 244, and a distal tip 246. While the instrument shaft 240 is linear in this example, in some embodiments one or more portions of the instrument shaft 240, or the entirety of the instrument shaft 240 can be curved. In some such embodiments, the curved portion(s) of the instrument shaft 240 are permanently curved. In some such embodiments, the curved portion(s) of the instrument shaft 240 are actuatable such that a clinician user of the instrument shaft 240 can control the shape of the portion to make it transition between being curved or linear.

In some embodiments, the instrument shaft 240 (or portions thereof) is constructed of a semi-flexible material or a malleable material. Such materials can be metals or polymers such as Pebax or Nylon, such that the instrument shaft 240 and its internal geometry would be easily curved by external forces. This would allow curvature of the instrument shaft 240 at the discretion of the clinician (manually or otherwise) without requiring specific manufacturing. Additionally this would allow curvature of the instrument shaft 240 to suit the angulation of the patient's ear canal anatomy, or reduce the likelihood of damage to distal anatomy such as the tympanic membrane. Steerable mechanisms could be constructed using polymer tubings to take advantage of the relatively short distance (e.g., in comparison to similar diameter neurovascular catheters which are often >120 cm long), while also allowing a tight bend radius. Other polymers used for the construction of the instrument shaft 240 can include, but are not limited to, HDPE, PEEK, PET, silicone, polyurethane, and others.

The proximal portion 242 is optional. In some embodiments, the proximal portion 242 is configured to add stiffness, column strength, and/or stability to the instrument shaft 240.

In some embodiments, the length of the instrument shaft 240 is in a range from about 30 mm to 90 mm, about 40 mm to 80 mm, about 50 mm to 80 mm, about 60 mm to 80 mm, or about 70 mm. In some embodiments, the diameter of the distal end portion 244 is in a range from about 0.02 mm to 1.1 mm, about 0.06 mm to 0.8 mm, about 0.1 mm to 0.7 mm, or about 0.4 mm to 0.6 mm. Accordingly, a ratio of the length of the instrument shaft 240 to the diameter of the distal end portion 244 can be in a range from about 400:1 to 50:1, about 300:1 to 100:1, about 200:1 to 100:1, or about 130:1 to 170:1.

In some embodiments, the proximal portion 242 has a larger diameter than the distal end portion 244. For example, in some embodiments the diameter of the proximal portion 242 is in a range from about 1 mm to 3 mm, or about 1.5 mm to 2.5 mm. The proximal portion 242 can have a length in a range from about 5 mm to 80 mm, about 10 mm to 70 mm, about 20 mm to 60 mm, or about 30 mm to 50 mm.

The otologic instrument 200 can include an end effector attached at the distal tip 246. Any type of end effector can be included. For example, FIGS. 14-30 depict various types non-limiting end effectors that can be included as part of the otologic instrument 200. Accordingly, the otologic instrument 200 can be configured to be used for multiple purposes such as, but not limited to, grasping, cutting, tearing, cauterizing, injecting, aspirating, irrigating, as an endoscope, and so on, and combinations thereof. Such end effectors could include an angled blade or inner ear knife, pick forceps or extendable pick with angle change, micro atraumatic suction, side biting scissors, round knife, middle ear knife (like a sickle), injection cannula, and any other instruments useful in otologic procedures.

In some embodiments, the distal end portion 244 (or a portion thereof) is actuatable, steerable, and/or deflectable. In some cases it is advantageous to have the steerable or deflectable distal end portion 244 controllably move the functionality off-axis from the adjacent proximal portion 242, especially in the middle ear 40 where the bony features of the middle ear block straight-line axis and creates blind corners. In some embodiments, the steerability or deflection of the distal end portion 244 allows opposing the angulation of the handle or curvature of the shaft anywhere between 90° to 270°, between 120° to 240°, between 150° to 210°, or between 170° to 190° from the angulation or curvature of the handle 210.

In some embodiments, the distal end portion 244 is deflectable and can have a minimum bend radius that is between about 2 mm to 8 mm. It can be envisioned that in the relatively "tight" space of the middle ear 40, having a bend radius for the distal end portion 244 that is between about 2 mm to 8 mm is advantageous. This is a tighter bend radius than typically achievable with varieties of laser cut metallic hypotubes. In some embodiments, having a concentric series of polymer tubes, with an inner tube with large cutouts (larger than required for hypotubes of steel or other metals) could allow preferential bending of the distal end portion 244 to such a tight bend radius that it is essentially kinking of the inner tube (material such as PEEK or PET). The outer tubes would be flexible materials and still allow fluid flow either to or from the distal tip portion 244 (such as Pebax or polyurethane), and a majority of polymers would predominantly recover their shape once force was removed (thereby facilitating removal of the distal tip). Other polymers could be HDPE, PEEK, PET, silicone, polyurethane, and others.

It some embodiments it would be advantageous to allow the radial rotation of the distal end portion 244 with respect to the angulation of the handle 210 or curvature of the proximal portion 242. Otologists are often left or right "handed," meaning having a preference for using specific tools with a given hand, and the left ear versus the right ear require different angles of approach. The ability to rotate actuation and curvature angles of the distal end portion 244 would facilitate otologists using instruments in their preferred hand. Additionally, this would allow the ability to navigate or steer around bends or corners depending on the target, without changing access site.

The otologic instrument 200 includes the angulation portion 230. The angulation portion 230 is disposed between the handle 210 and the instrument shaft 240.

Accordingly, the longitudinal axis of the handle 210 and the longitudinal axis of the instrument shaft 240 can be non-linear in relation to each other, or arranged at a non-zero angle in relation to each other. In some embodiments, the angle defined between the longitudinal axis of the handle 210 and the longitudinal axis of the instrument shaft 240 is in a range from about 0° to 90°, about 10° to 70°, about 20° to 50°, or about 30° to 40°.

In some embodiments, the angulation portion 230 is configured such that the angle defined between the longitudinal axis of the handle 210 and the longitudinal axis of the instrument shaft 240 is a fixed or constant angle. In particular embodiment, the angulation portion 230 is configured to be adjustable such that the angle defined between the longitudinal axis of the handle 210 and the longitudinal axis of the instrument shaft 240 is selectively adjustable by a clinician user of the otologic instrument 200.

The angulation between the longitudinal axis of the handle 210 and the longitudinal axis of the instrument shaft 240 provided by the angulation portion 230 facilitates improved access down the ear canal 20, as well as improved external or microscope-based visualization (currently the most common visualization used by otologists). It also enables the use of two or more instruments 200 in the ear canal 20 simultaneously.

The otologic instrument 200 also includes the actuation mechanism 220. In the depicted embodiment, the otologic instrument 200 includes a single actuation mechanism 220. In some embodiments, the otologic instrument 200 includes two or more actuation mechanisms (which can be of the same type of mechanism or of differing types of mechanisms). The depicted actuation mechanism 220 is configured to be actuated by compressing the actuation mechanism 220. In some embodiments, other types of actuations mechanisms 220 can be included as part of the otologic instrument 200. For example, the actuations mechanisms 220 can be one or more of a button, trigger, slider, rotary knob, foot pedal, a valve, and the like, and combinations thereof.

The otologic instrument 200 also includes the handle 210. In some embodiments, the handle 210 and any actuation mechanisms 220 may be reduced in diameter to approximately 4 mm to 8 mm to improve access and visualization.

The otologic instrument 200 can include markings along the handle 210 to indicate to the clinician 1 the direction of the steerability of the distal end portion 244, actuation of the distal end portion 244 or end effector, and/or deflectability of the distal end portion 244, or other portions of the otologic instrument 200. Some embodiments can have additional or combination markings on the proximal portion 242 and/or the distal end portion 244 to aid in depth perception, which is advantageous when using an endoscope as one of the visualization instruments (which does not have binocular view or depth perception).

Figure 8:
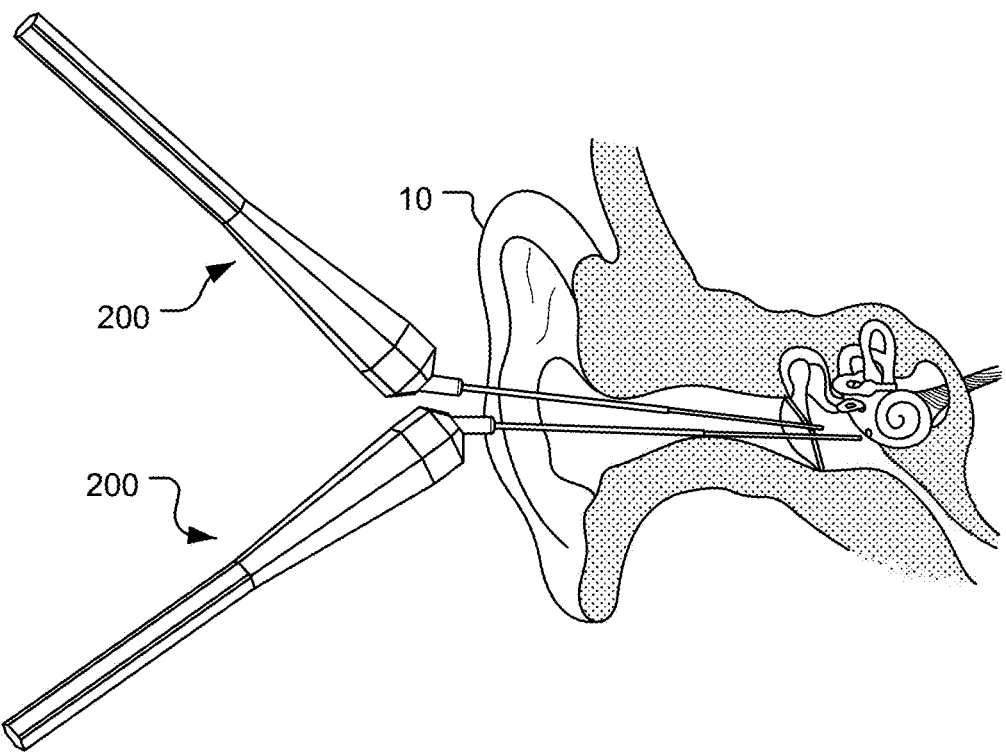
FIGS. 8-10 show two of the example otology instruments of FIG. 6 in use during a medical procedure for treating ear disorders as described herein.
Figure 9:
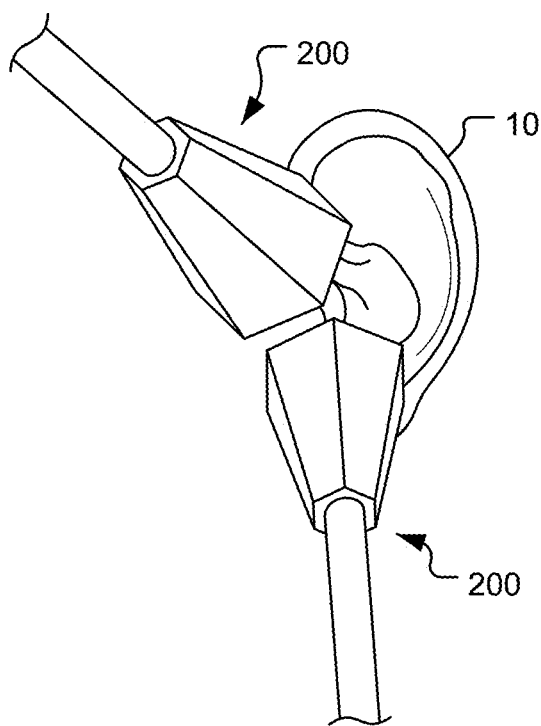
Figure 10:
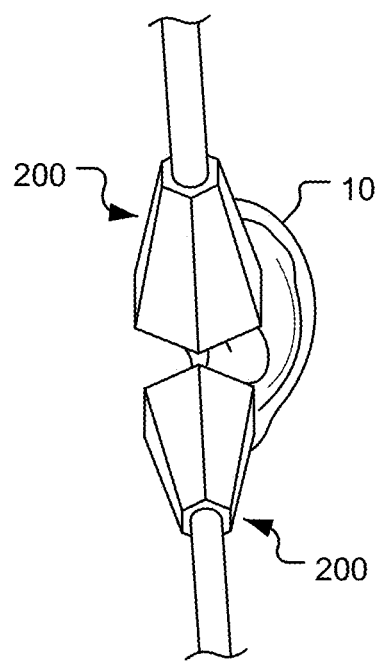

Referring also to FIGS. 8-10, here various example configurations in which two of the otologic instrument 200 are being used concurrently are depicted. It is readily apparent from these views that the angulation between the longitudinal axis of the handle 210 and the longitudinal axis of the instrument shaft 240 is advantageous for spacing apart the handles 210 such that the instruments 200 are individually manipulatable without interference from each other.

Figure 7:
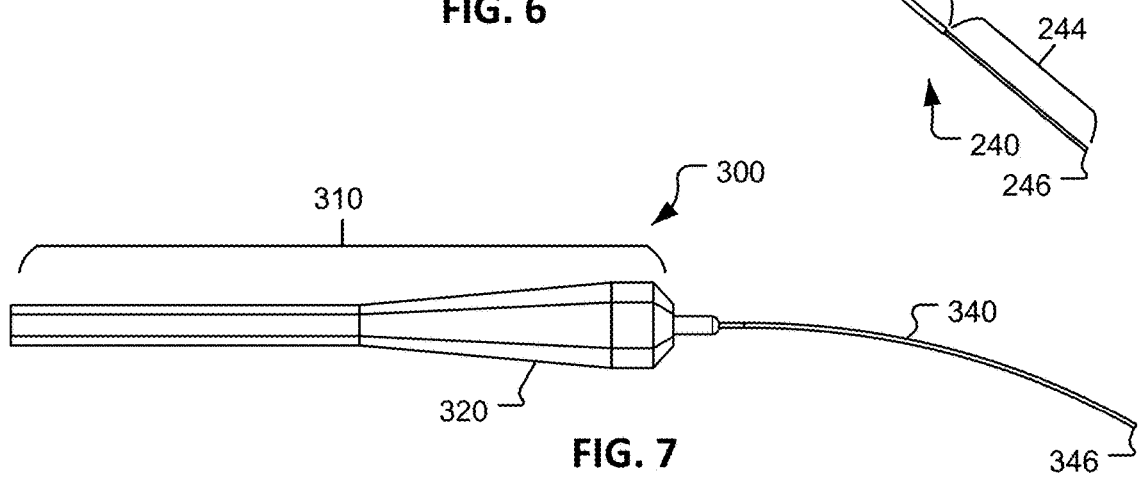
FIG. 7 shows another example otology instrument in accordance with some embodiments.

Referring to FIG. 7, another example otologic instrument 300 is configured to facilitate its use, as described further below, in a manner that facilitates direct visualization and/or the use of two otologic instruments 300 concurrently. The otologic instrument 300 includes a handle 310, an actuation mechanism 320, and an instrument shaft 340. The actuation mechanism 320 is coupled to the handle 310, or comprises a portion of the handle 310. The instrument shaft 340 is coupled to and distally extends from the actuation mechanism 320 or the handle 310. The otologic instrument 300 can be reusable or disposable.

Any of the features of the otologic instrument 200 described above can be incorporated with the design of the otologic instrument 300. Also, any of the features of the otologic instrument 300 can be incorporated with the design of the otologic instrument 200. Accordingly, such hybrid otologic instruments are envisioned and are encompassed in the scope of this disclosure. The materials of construction of the otologic instrument 300 can be the same as those described above in reference to the otologic instrument 200. The sizes of the components of the otologic instrument 300 can be the same as the sizes of the components of the otologic instrument 200 as described above.

In some embodiments, the longitudinal axis of the handle 310 and the longitudinal axis of a proximal-most portion of the instrument shaft 340 are collinear. As the instrument shaft 340 extends distally, the axis of the instrument shaft 340 is curved, or is angled in relation to the axis of the handle 310. This arrangement moves the handle 310 off-axis from the distal portions of the instrument shaft 340. This creates potentially the possibility of even further moving the handle 310 out of the viewing field, thereby dramatically improving the ability to visualize externally down the ear canal 20 and facilitating simultaneous use of two instruments 300 without their handles 310 interacting with each other. Additionally, a gentle curvature of the instrument shaft 340 may enable actuation mechanisms that require tight tolerances or predominantly coaxial structures within the shaft 340. In some embodiments, such a longitudinal curvature of the instrument shaft 340 can cause the distal tip 346 to be about 0.0 cm to 5.0 cm, about 1.0 cm to 5.0 cm, or about 2.0 cm to 5.0 cm off-axis from the longitudinal axis of the handle 310.

Any type of end effector can be incorporated by the otologic instrument 300 at the distal tip 346. For example, FIGS. 14-30 depict various types non-limiting end effectors that can be included as part of the otologic instrument 300. Accordingly, the otologic instrument 300 can be configured to be used for multiple purposes such as, but not limited to, grasping, cutting, tearing, cauterizing, injecting, aspirating, irrigating, as an endoscope, and so on, and combinations thereof. Such end effectors could include an angled blade or inner ear knife, pick forceps or extendable pick with angle change, micro atraumatic suction, side biting scissors, round knife, middle ear knife (like a sickle), injection cannula, and any other instruments useful in otologic procedures.

In some embodiments, the instrument shaft 340 (or a portion thereof) is actuatable, steerable, and/or deflectable. In some cases, it is advantageous to have the steerable or deflectable instrument shaft 340 controllably move the functionality off-axis from the handle 310, especially in the middle ear 40 where the bony middle ear structures block straight-line axis and creates blind corners. In some embodiments, the curvature, the steerability, or the deflection of the instrument shaft 340 allows the distal end of the instrument shaft 340 to extend anywhere between 10° to 50°, between 20° to 40°, between 20° to 30°, or between 10° to 30° in relation to the longitudinal axis of the handle 210.

The otologic instrument 300 also includes the actuation mechanism 320. In the depicted embodiment, the otologic instrument 300 includes a single actuation mechanism 320. In some embodiments, the otologic instrument 300 includes two or more actuation mechanisms (which can be of the same type of mechanism or of differing types of mechanisms). The depicted actuation mechanism 320 is configured to be actuated by compressing the actuation mechanism 320. In some embodiments, other types of actuations mechanisms 320 can be included as part of the otologic instrument 300. For example, the actuations mechanisms 320 can be one or more of a button, trigger, slider, rotary knob, foot pedal, a valve, and the like, and combinations thereof.

The otologic instrument 300 also includes the handle 310. In some embodiments, the handle 310 and any actuation mechanisms 320 may be reduced in diameter to approximately 4 mm to 8 mm to improve access and visualization.

The otologic instrument 300 can include markings along the handle 310 to indicate to the clinician 1 the direction of the curvature of the instrument shaft 340, actuation of the instrument shaft 340 or end effector, and/or deflectability of the instrument shaft 340, or other portions of the otologic instrument 300. Some embodiments can have additional or combination markings on the instrument shaft 340 to aid in depth perception, which is advantageous when using an endoscope as one of the visualization instruments (which does not have binocular view or depth perception).

Figure 11:
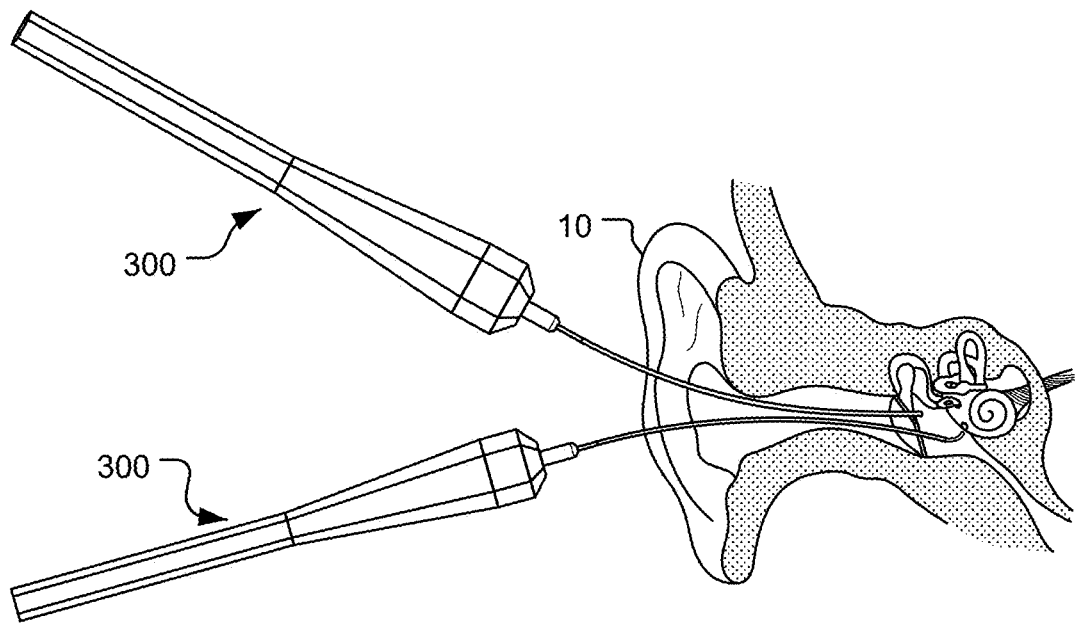
FIGS. 11 and 12 show two of the example otology instruments of FIG. 7 in use during a medical procedure for treating ear disorders as described herein.
Figure 12:
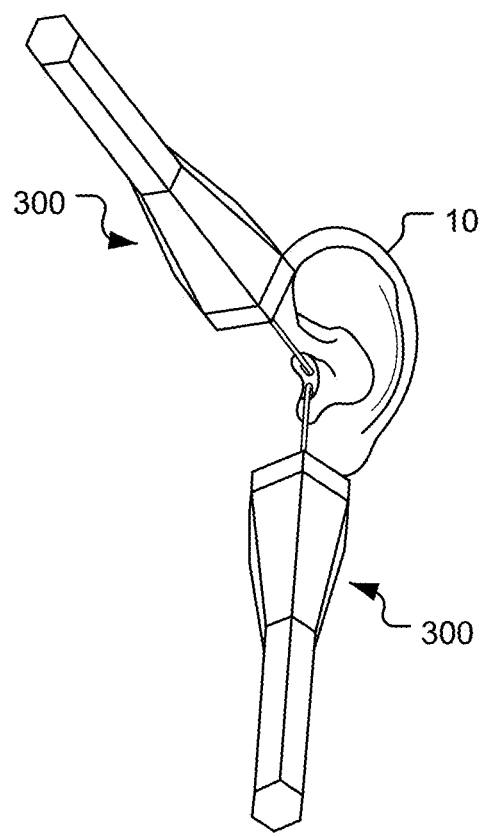

Referring also to FIGS. 11 and 12, here various example configurations in which two of the otologic instrument 300 are being used concurrently are depicted. It is readily apparent from these views that the curvature of the instrument shaft 340 is advantageous for spacing apart the handles 310 such that the instruments 300 are individually manipulatable without interference from each other.

Figure 13:
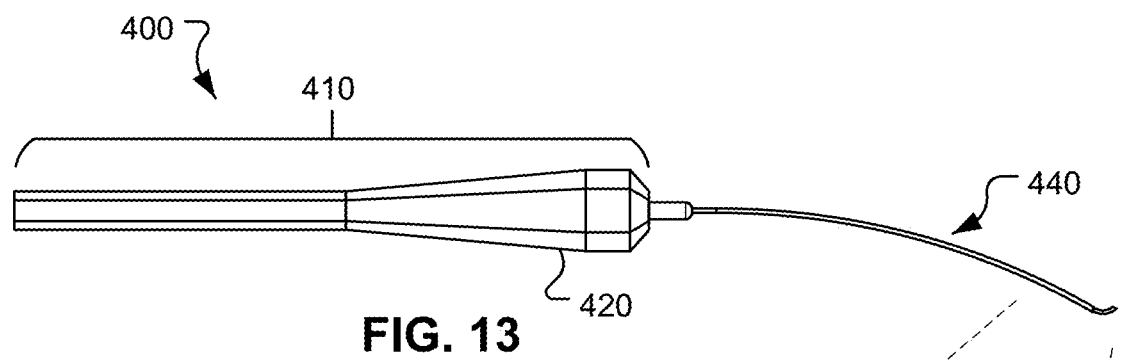
FIG. 13 shows another example otology instrument in accordance with some embodiments.
Figure 14:
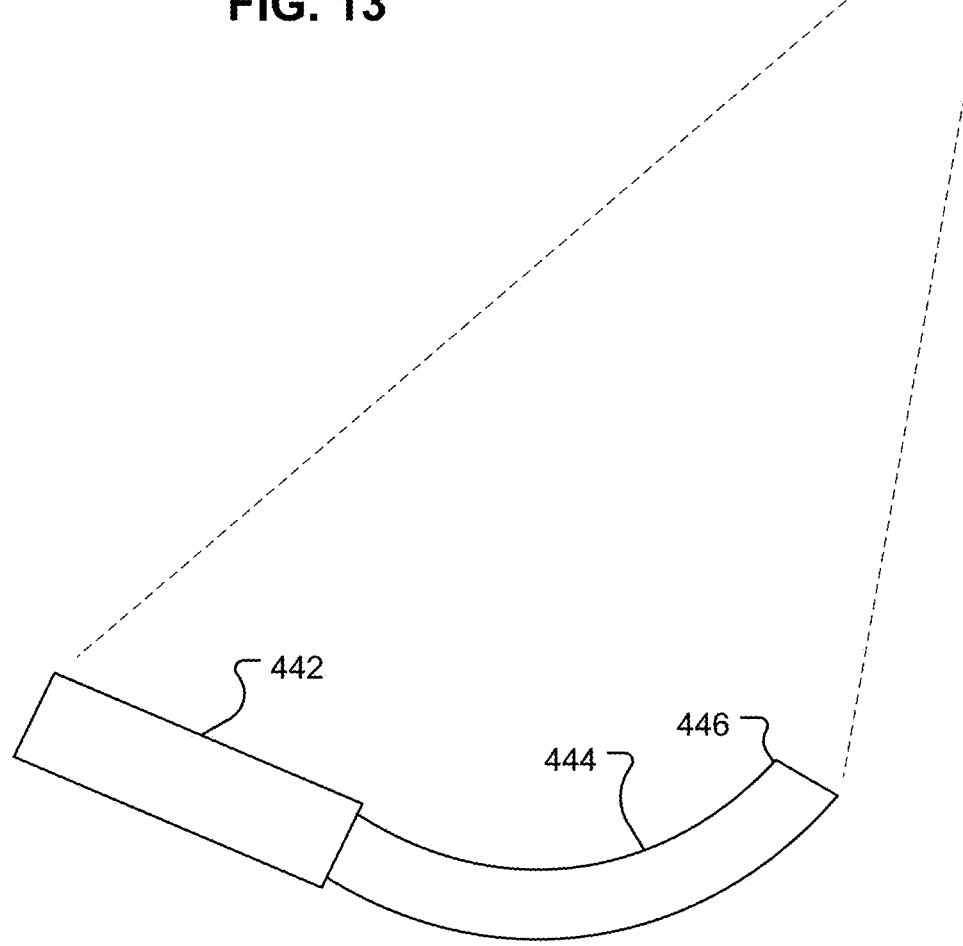
FIG. 14 shows an enlarged view of a distal end portion of the example otology instrument of FIG. 13.

Referring to FIGS. 13 and 14, another example otologic instrument 400 is configured to facilitate its use, as described further below, in a manner that facilitates direct visualization and/or the use of two otologic instruments 400 concurrently. The otologic instrument 400 includes a handle 410, an actuation mechanism 420, and an instrument shaft 440. The actuation mechanism 420 is coupled to the handle 410, or comprises a portion of the handle 410. The instrument shaft 440 is coupled to and distally extends from the actuation mechanism 420 and/or the handle 410. The otologic instrument 400 can be reusable or disposable.

Any of the features of the otologic instruments 200 and 300 described above can be incorporated with the design of the otologic instrument 400. Also, any of the features of the otologic instrument 400 can be incorporated with the design of the otologic instruments 200 and 300. Accordingly, such hybrid otologic instruments are envisioned and are encompassed in the scope of this disclosure. The materials of construction of the otologic instrument 400 can be the same as those described above in reference to the otologic instruments 200 and 300. The sizes of the components of the otologic instrument 400 can be the same as the sizes of the components of the instruments 200 and 300 as described above.

The instrument shaft 440 includes an outer sleeve member 442 and an inner deflectable member 444. The outer sleeve member 442 can be curved (like the instrument shaft 340 described above). In some embodiments, the inner deflectable member 444 can be slidably disposed within the outer sleeve member 442. The inner deflectable member 444 includes a distal tip 446.

The inner deflectable member 444 can be controllably deflected by the clinician 1. In some embodiments, the inner deflectable member 444 is selectively deflectable and can be deflected to attain a minimum bend radius that is between about 2 mm to 8 mm. It can be envisioned that in the relatively "tight" space of the middle ear 40, having a bend radius for the inner deflectable member 444 that is between about 2 mm to 8 mm is advantageous. This is a tighter bend radius than typically achievable with varieties of laser cut metallic hypotubes. In some embodiments, having a concentric series of polymer tubes, with an inner tube with large cutouts (larger than required for hypotubes of steel or other metals) could allow preferential bending of the inner deflectable member 444 to such a tight bend radius that it is essentially kinking of the inner tube (material such as PEEK or PET).

The otologic instrument 400 can include an end effector attached at the distal tip 446. Based upon the disclosure herein, it will be clear that a variety of types of end effector can be included, especially those sized and structured for use in the middle ear. For example, FIGS. 15-30 depict various types non-limiting end effectors that can be included as part of the otologic instrument 400. Accordingly, the otologic instrument 400 can be configured to be used for multiple purposes such as, but not limited to, grasping, cutting, tearing, cauterizing, injecting, aspirating, irrigating, as an endoscope, and so on, and combinations thereof. Such end effectors could include an angled blade or inner ear knife, pick forceps or extendable pick with angle change, micro atraumatic suction, side biting scissors, round knife, middle ear knife (like a sickle), injection cannula, and any other instruments useful in otologic procedures.

Figure 15:
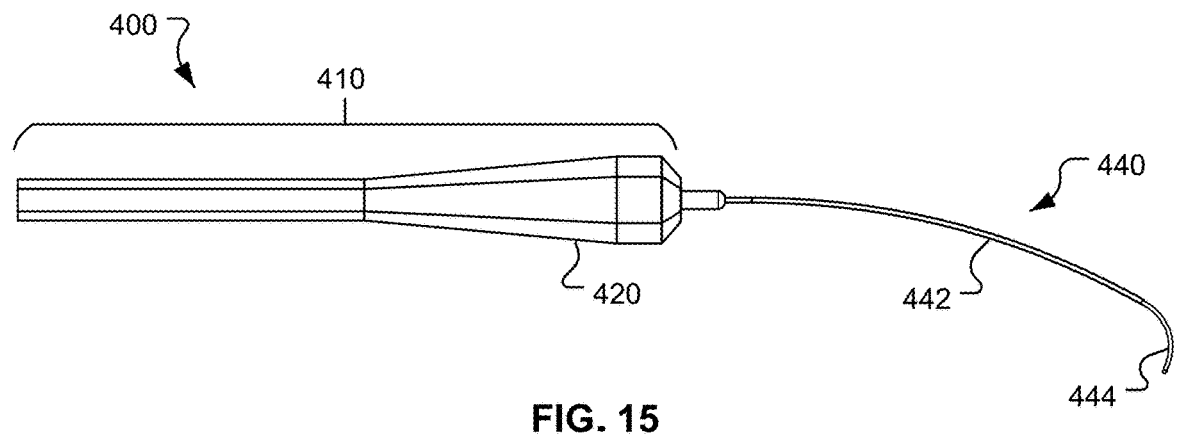
FIG. 15 shows the otology instrument of FIG. 13 in a first example configuration.
Figure 16:
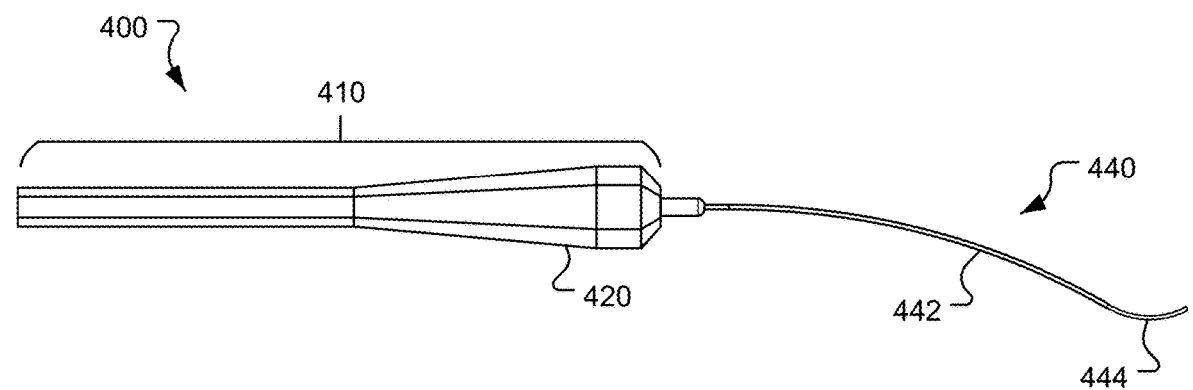
FIG. 16 shows the otology instrument of FIG. 13 in a second example configuration.

Referring also to FIGS. 15 and 16, in some embodiments the inner deflectable member 444 is controllably rotatable relative to the outer sleeve member 442 and the handle 410. Accordingly, the clinician 1 can rotate the inner deflectable member 444 to adjust the radial extension direction of the inner deflectable member 444 relative to the longitudinal axis of the handle 410 over a wide range of angles (e.g., 90°, 180°, 270°, 360°, or anywhere therebetween).

In the configuration of FIG. 15, the curvatures of the outer sleeve member 442 and the inner deflectable member 444 are in the same direction and are therefore additive. In some embodiments, the steerability or deflection of the distal end portion 244 allows aligning with the angulation of the handle or curvature of the shaft anywhere between 60° to 300° from the angulation or curvature of the handle 210. In contrast, in the configuration of FIG. 16, the curvatures of the outer sleeve member 442 and the inner deflectable member 444 are in opposite directions. Accordingly, it can be envisioned that by rotating the inner deflectable member 444 relative to the longitudinal axis of the handle 410, and by deflecting the inner deflectable member 444, a broad range of configurations of the instrument shaft 440 are possible.

In some embodiments, the otologic instrument 400 includes markers along the handle 410 to indicate to the clinician 1 the rotary direction of radial extension direction of the inner deflectable member 444 and/or the bend radius of the inner deflectable member 444. Some embodiments can have additional or combination markings on the instrument shaft 440 to aid in depth perception, which is advantageous when using an endoscope as one of the visualization instruments (which does not have binocular view or depth perception).

FIGS. 17-30 illustrate various types of end effectors that can be incorporated in any of the otologic instruments described herein. It should be understood that these end effectors are merely examples and that other types of end effectors can also be incorporated with any of the otologic instruments described above.

Figure 17:
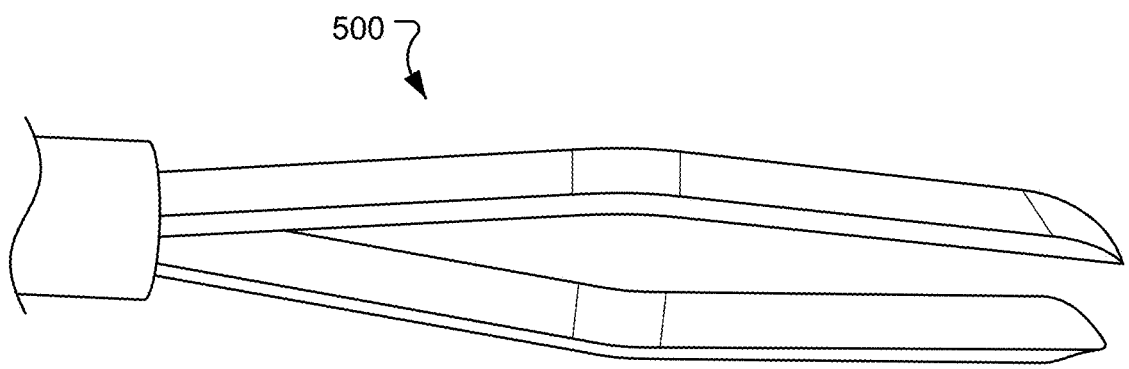
FIG. 17 shows an example end effector that can be incorporated in the otology instruments described herein.

FIG. 17 illustrates an example grasping device 500 that can be incorporated in any of the otologic instruments described herein. One or both of the jaws of the grasping device 500 can be movably actuated by the clinician 1 to grasp tissue between the jaws.

Figure 18:
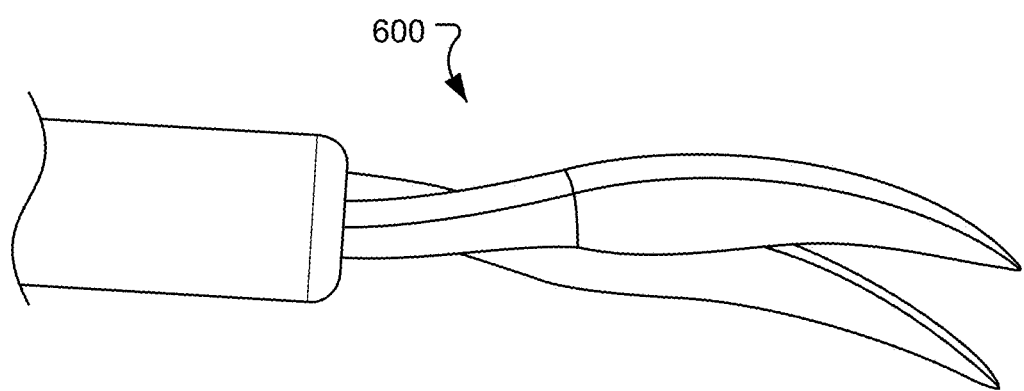
FIG. 18 shows another example end effector that can be incorporated in the otology instruments described herein.

FIG. 18 illustrates an example cutting device 600 that can be incorporated in any of the otologic instruments described herein. The cutting device 600 includes curved blades that can be actuated by the clinician 1 to shear tissue. The tips of the blades can also be used to puncture and/or manipulate tissue.

Figure 19:
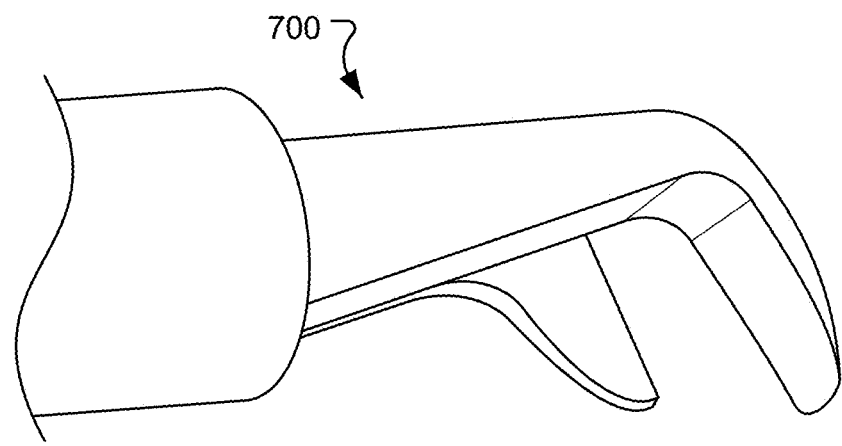
FIG. 19 shows another example end effector that can be incorporated in the otology instruments described herein.

FIG. 19 illustrates an example side biting scissors 700 that can be incorporated in any of the otologic instruments described herein. The side biting scissors 700 includes laterally extending blades that can be actuated by the clinician 1 to shear tissue. The tips of the blades can also be used to puncture and/or manipulate tissue.

Figure 20:
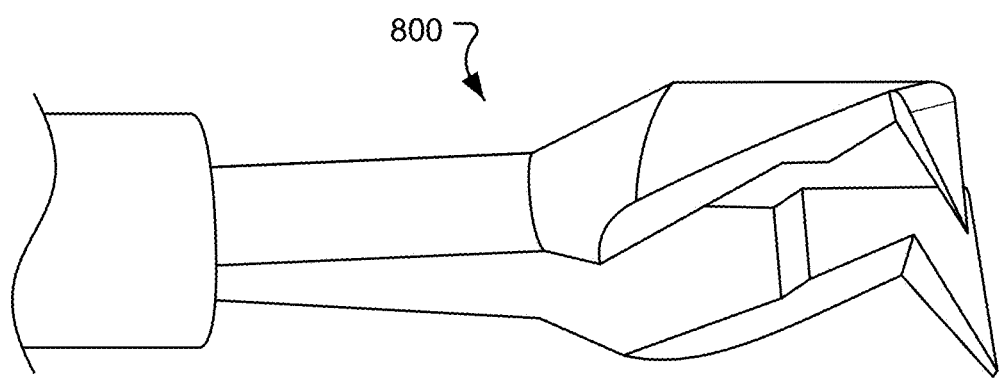
FIG. 20 shows another example end effector that can be incorporated in the otology instruments described herein.

FIG. 20 illustrates an example pick forceps 800 that can be incorporated in any of the otologic instruments described herein. One or both of the jaws of the pick forceps 800 can be movably actuated by the clinician 1 to grasp tissue between the jaws. The tips of the jaws can also be used to puncture and/or manipulate tissue.

Figure 21:
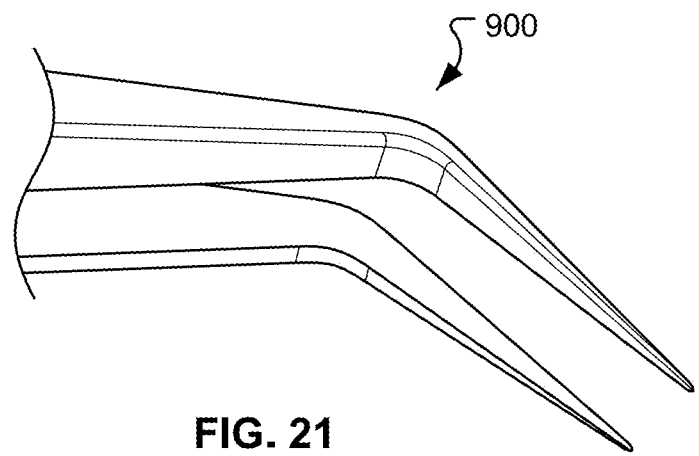
FIG. 21 shows another example end effector that can be incorporated in the otology instruments described herein.

FIG. 21 illustrates another example pick forceps 900 that can be incorporated in any of the otologic instruments described herein. One or both of the jaws of the pick forceps 900 can be movably actuated by the clinician 1 to grasp tissue between the jaws. The tips of the jaws can also be used to puncture and/or manipulate tissue.

Figure 22A:
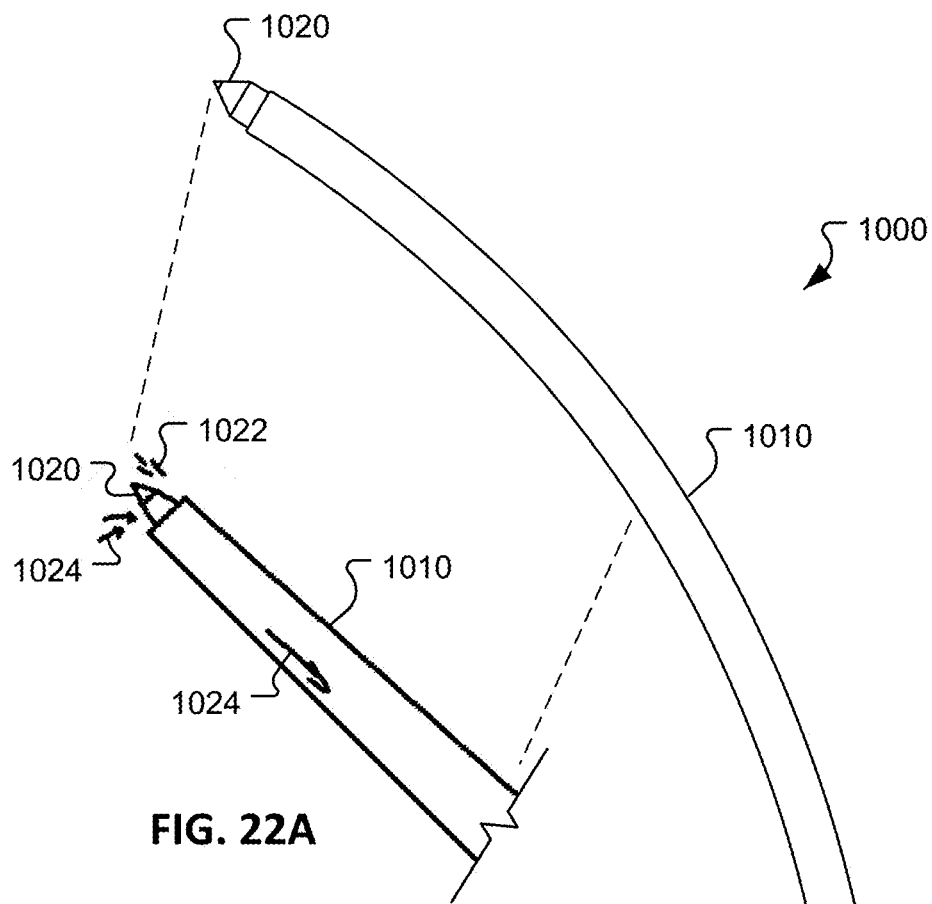
FIG. 22A shows an alternative design of the instrument of FIG. 22.
Figure 22:
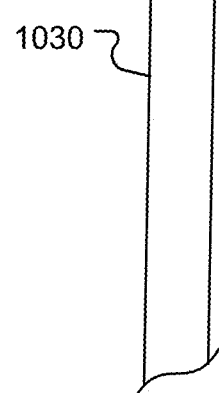
FIG. 22 shows another example end effector that can be incorporated in the otology instruments described herein.

FIG. 22 illustrates an example coaxial bipolar diathermy instrument 1000 that can be incorporated in any of the otologic instruments described herein. The coaxial diathermy instrument 1000 includes a probe 1010 and a distal tip 1020 that includes an electrode to deliver heat. With the use of the coaxial principle, the current flows only at the probe's end surfaces. It allows a functionality that is essentially an intense heat to be localized at the very distal tip 1020 of the probe 1010. It's small size and end-on coagulation effect, and when used with a low-frequency diathermy unit, allow such a probe to be used safely in close proximity to delicate tissues. Bipolar diathermy instruments are used in the canal and externally in otology but are, and previously have been, too large and imprecise for middle ear surgery. Extant diathermy instruments in the otology field have not been used in middle ear procedures for a variety of reasons, including the difficulty in access to the middle or inner ear region, and because of the bony structures of the middle ear blocking straight-line angle of attack to the desired target.

In some embodiments, the probe 1010 can be deflectable or steerable (as described above) for functionality off-axis from the adjacent shaft 1030. In other embodiments, an aspiration feature could be included in the same instrument to remove loose blood or thin clots from actively bleeding vessels, and then coagulate them immediately. This coaxial diathermy instrument 1000 is highly advantageous and enables a whole new functionality for otologic procedures.

FIG. 22A depicts an optional modification of the coaxial bipolar diathermy instrument 1000. Diathermy on its own is a useful modality for surgical intervention that is not currently used in otology; whether in mastoid/open access procedures, external ear canal, middle ear, or inner ear applications. The addition of other functionality to diathermy would increase the usefulness even further than expected.

One additional, useful functionality that can optionally be added to the coaxial bipolar diathermy instrument 1000 is adding lighting (as depicted by light rays 1022). The diathermy instrument 1000 can have a light source mounted at the distal tip, or a fiber optic that carries light to the distal tip. Adequate lighting can be problematic in otologic procedures, especially if the handles of the instruments in use are blocking a light source. The middle ear and surrounding anatomy are made up of many small complex structures that create corners that block visualization and lighting as well, and having on-board lighting with the diathermy probe instrument 1000 would greatly enhance its range of use as well as ease of use. The ability to control a light source proximal to the target tissue also minimizes the potential for glare created from reflection off other surfaces, such as the tympanic membrane. Movements of the light source during operation can also cast shadows, allowing for more ready identification of anatomic structures.

Another additional useful functionality that can optionally be added to the coaxial bipolar diathermy instrument 1000 is aspiration (as depicted by arrows 1024). Diathermy would likely be predominantly useful for controlling bleeds as a way to cauterize micro-vessels in the middle ear cavity or in the ear canal. Adding aspiration functionality would enable "one handed" ability to cauterize vessels while clearing out the surgical space of blood and other cauterized tissue. This two-part ability to manage bleeding would greatly ease the clinicians' ability to quickly control bleeds and thereby minimize procedure time, minimize instrument switch-outs and associated chances at collateral tissue damage, reduce personnel required and number of hands in the surgical space, and overall ease a burdensome task encountered in in most surgical procedures.

The use of the coaxial bipolar diathermy instrument 1000 in combination with built-in lighting 1022 and/or aspiration 1024 would create a one-handed instrument 1000 well suited to use in otologic procedures with value greater than the expected sum of the individual functionalities.

FIGS. 23 and 24a-24c illustrate an example pneumatic aspirating cutter 1100 that can be incorporated in any of the otologic instruments described herein. The pneumatic aspirating cutter 1100 includes an outer shaft 1110 and an inner reciprocating shaft 1120. The inner reciprocating shaft 1120 reciprocates proximally and distally within the lumen defined by the outer shaft 1110. Accordingly, as depicted in FIGS. 24a-24c tissue can be cut between the outer shaft 1110 and the inner reciprocating shaft 1120 (e.g., like a "guillotine" blade cutter). When portions of tissue are cut, the tissue portions can be aspirated through pneumatic aspirating cutter 1100 as shown.

The pneumatic aspirating cutter 1100 can be useful, for example, for removing middle ear tissue and freshening edges of a tympanic membrane perforation in a tympanoplasty procedure (tympanic membrane repair procedure). During tympanoplasty, the edges of the existing tympanic membrane perforation are first "freshened" by removing tissue around the perimeter of the perforation. Currently there is no precise instrument for performing this procedure and typically more tissue is removed than necessary, resulting in a larger perforation than necessary, further complicating the subsequent patching procedure. The small pneumatic "guillotine" blade cutter with aspiration provided by the pneumatic aspirating cutter 1100, could ensure more precise cutting of the perimeter. This can also be combined with liquid infusion or flooding of the middle ear and/or outer ear canal. The pneumatic aspirating cutter 1100 can also have utility in removing membranes and fibrous tissues in the middle ear.

In the case of the axially reciprocating blade of the inner reciprocating shaft 1120, the port defined by the outer shaft 1110 is most ideally located on the side of the outer shaft 1110 so that target tissue is approached with the side of the instrument tip ("side cutting"). For example, this orientation can be preferred when debriding the perimeter of a tympanic membrane perforation in preparation for graft placement or repair. A side cutting port can also be ideal for removal of cerumen from the ear canal wall.

Figure 25:
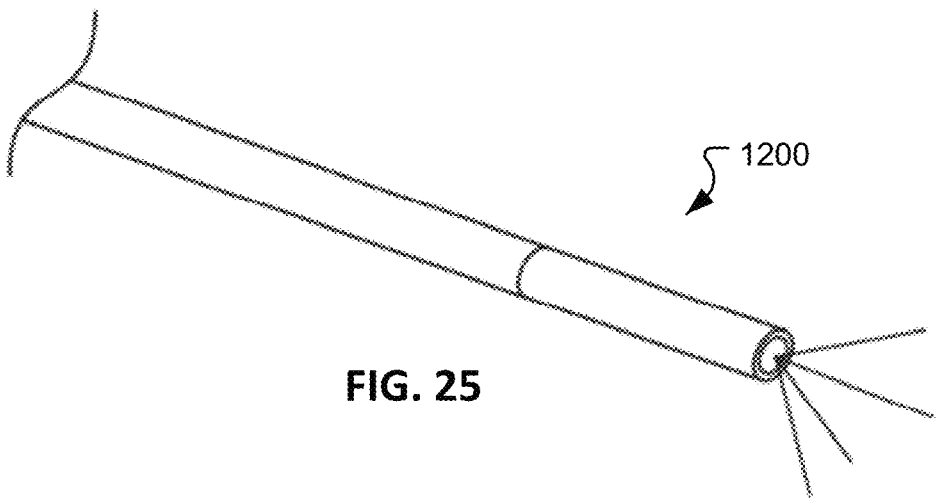
FIG. 25 shows another example end effector that can be incorporated in the otology instruments described herein.

FIG. 25 illustrates an example endoscope 1200 or light source 1200 that can be incorporated in any of the otologic instruments described herein.

Figure 26:
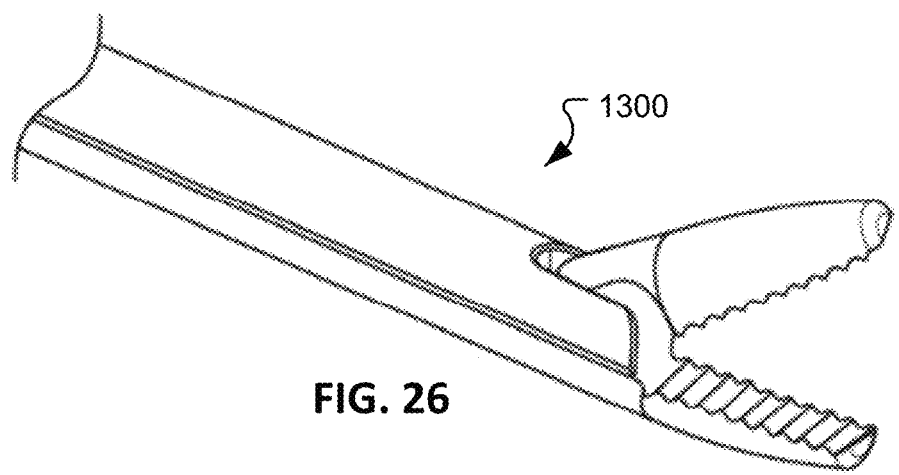
FIG. 26 shows another example end effector that can be incorporated in the otology instruments described herein.

FIG. 26 illustrates another example grasping device 1300 that can be incorporated in any of the otologic instruments described herein.

Figure 27:
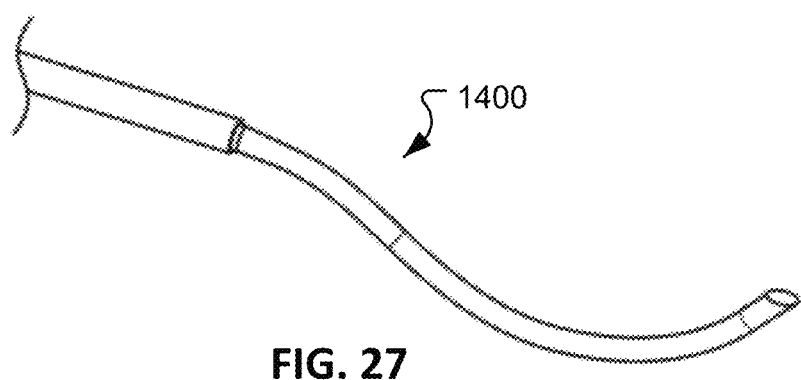
FIG. 27 shows another example end effector that can be incorporated in the otology instruments described herein.

FIG. 27 illustrates an example injection instrument 1400 that can be incorporated in any of the otologic instruments described herein. The distal end portion of the injection instrument 1400 can be steerable/deflectable or can have a naturally curved shape that manifest as the distal end portion emerges from the proximal sleeve in which the distal end portion is slidably disposed.

Figure 28:
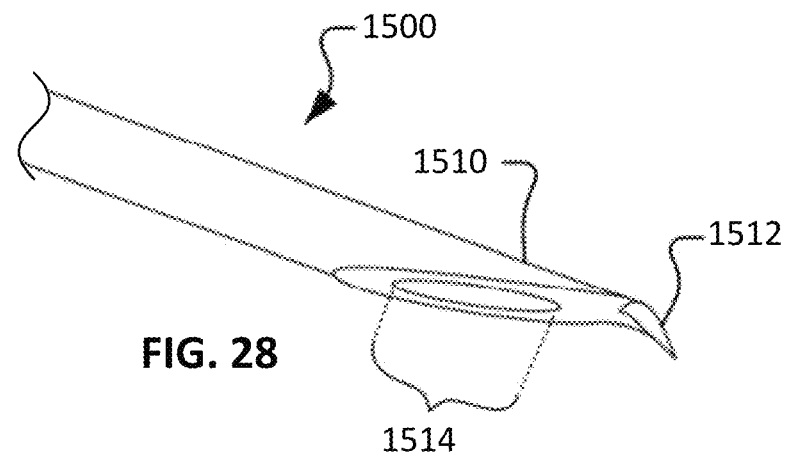
FIG. 28 shows another example end effector that can be incorporated in the otology instruments described herein.

FIG. 28 illustrates an example aspiration instrument 1500 that can be incorporated in any of the otologic instruments described herein. In some embodiments, the distal end portion 1510 of the aspirating device 1500 can include a pointed tip member 1512 and an aspiration port 1514. The pointed tip member 1512 can be used by the clinician 1 for various purposes such as, but not limited to, puncturing tissue, tearing tissue, dissecting tissues, retracting tissues, and the like. The aspiration port 1514 can be used by the clinician 1 for applying suction to perform various tasks such as, but not limited to, removal of fluids, removal of particles, vacuum attachment to tissues for dissecting tissues, retracting tissues, stretching/tearing tissues, and the like.

Figure 29:
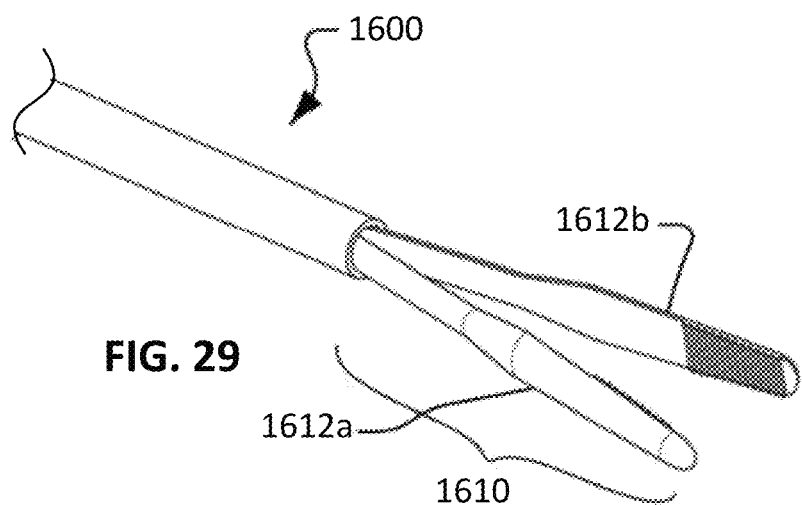
FIG. 29 shows another example end effector that can be incorporated in the otology instruments described herein.

FIG. 29 illustrates an example spreader device 1600 that can be incorporated in any of the otologic instruments described herein. In some embodiments, the distal end portion 1610 of the spreader device 1600 includes a first splaying member 1612a and an opposed second splaying member 1612b. The splaying members 1612a-b can be actuated by the clinician 1 to open/separate as shown in FIG. 29, and to close. The splaying members 1612a-b can thereby be used by the clinician 1 for various purposes such as, but not limited to, separating tissues, tearing tissue, dissecting tissues, pulling tissue, retracting tissues, and the like. In some embodiments, the distal tips of the splaying members 1612a-b can be blunt, atraumatic tips as depicted.

Figure 30:
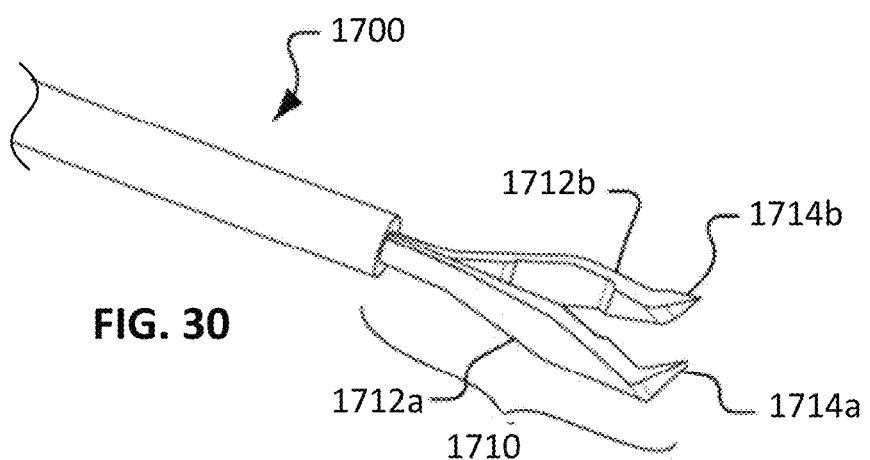
FIG. 30 shows another example end effector that can be incorporated in the otology instruments described herein.

FIG. 30 illustrates another example spreader device 1700 that can be incorporated in any of the otologic instruments described herein. The spreader device 1700 can be used to spread and tear open tissues such as the pseudomembrane in a manner that is very similar to that of the spreader device 1600 described above. However, in contrast to the blunt, atraumatic tips of the splaying members 1612a-b, the splaying members 1712a and 1712b of the spreader device 1700 include pointed tip members 1714a and 1714b, respectively. The pointed tip members 1714a-b, which can extend laterally at an angle from the axis of the spreader device 1700 as shown, can be used to puncture tissues, such as the pseudomembrane. Thereafter, the splaying members 1712a and 1712b can be distally advanced and then actuated opened (as shown in FIG. 30) by the clinician 1 to spread apart the pseudomembrane so that access to the round window is obtained (e.g., access to the round window niche and to the round window membrane).

While the spreader device 1700 includes splaying members 1712a and 1712b with the pointed tip members 1714a and 1714b extending angularly laterally, in some embodiments a side-biting scissors can be additional or alternatively used for the procedures described herein. Such a side-biting scissors can include two blades that are pivotable in relation to each other to shear tissue therebetween. In some embodiments, the pair of blades (or end portions thereof) can extend laterally at an angle (e.g., between 30° to 60°, or 20° to 80°, without limitation) from the axis of the scissors.

Other types of instruments, end effectors, and devices for delivering various other otologic treatment modalities are also envisioned and within the scope of this disclosure. For example, an ultrasonic instrument for bone or tissue removal (e.g., cholesteatoma) can be incorporated in any of the otologic instruments described herein. That is, a small gauge ultrasonic instrument equipped with suction and infusion to clear debris could be used to clear small areas of bone adjacent to the facial nerve and other delicate structures. Such an instrument could be used to help debride the bone of soft tissue, as in the case of cholesteatoma removal. The ability of the instrument to be "tuned" to remove specific tissue densities would be highly advantageous for improving the selectivity of tissue removal in cholesteatoma removal.

In addition, a laser instrument can be incorporated in any of the otologic instruments described herein. Laser-based methods are a useful modality for surgical intervention that is only in limited use currently in otology. Green laser can be particularly useful because it applies heat typically only where there is loose/exposed blood (due to the color of blood), which allows it to heat and cauterize blood without damaging underlying or adjacent tissue. These instruments have seen limited use in otology for a variety of reasons, including the difficulty in accessing the middle or inner ear region, and because of the bony middle ear structures block straight-line angle of attack to the desired target. In some embodiments, a functional tip laser probe with a tip that can be actuated to generate steerability or functionality off-axis from the adjacent shaft would be highly advantageous and enable a whole new functionality for otologic procedures.

In all of the above instrument embodiments, any of the functional end effectors, handle angulations, shaft curves or angulations, markings, actuation mechanisms, steerability mechanisms, deflectability mechanisms, and any other features described above may be combined in any variety of permutations and embodiments.

Figure 31:
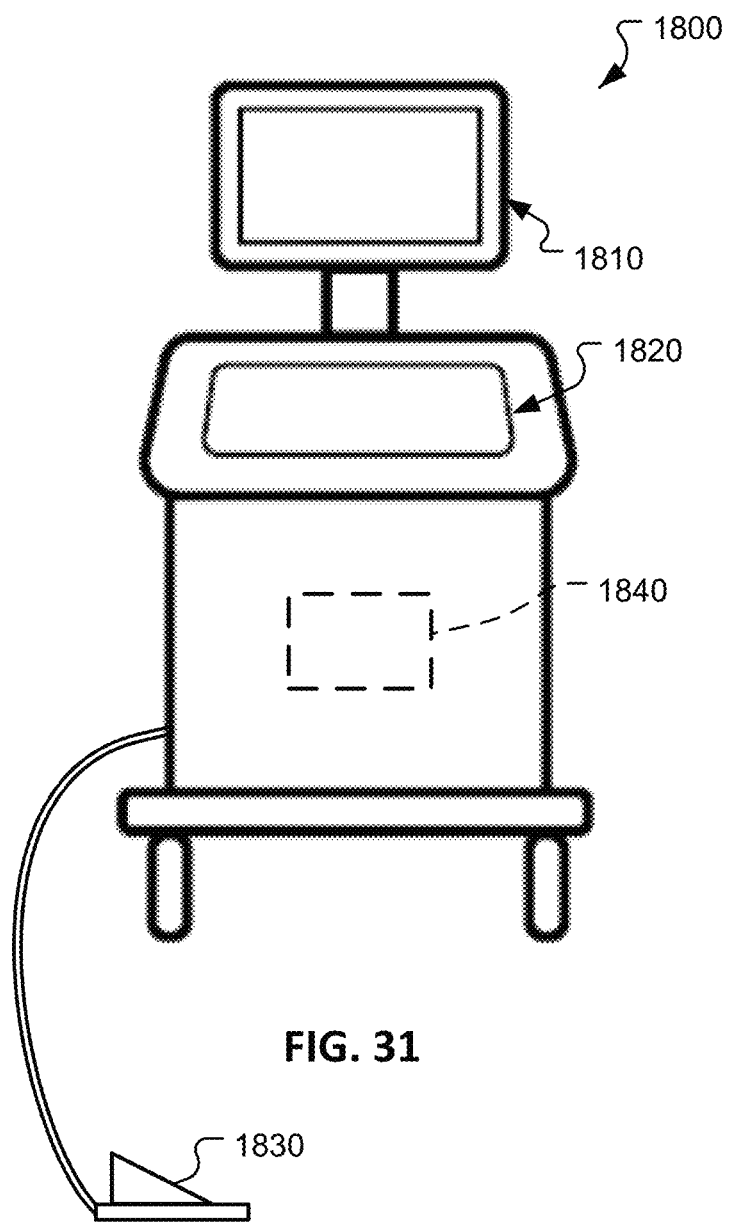
FIG. 31 depicts an example console system that can be used for otology procedures in accordance with some embodiments.
Figure 37A:
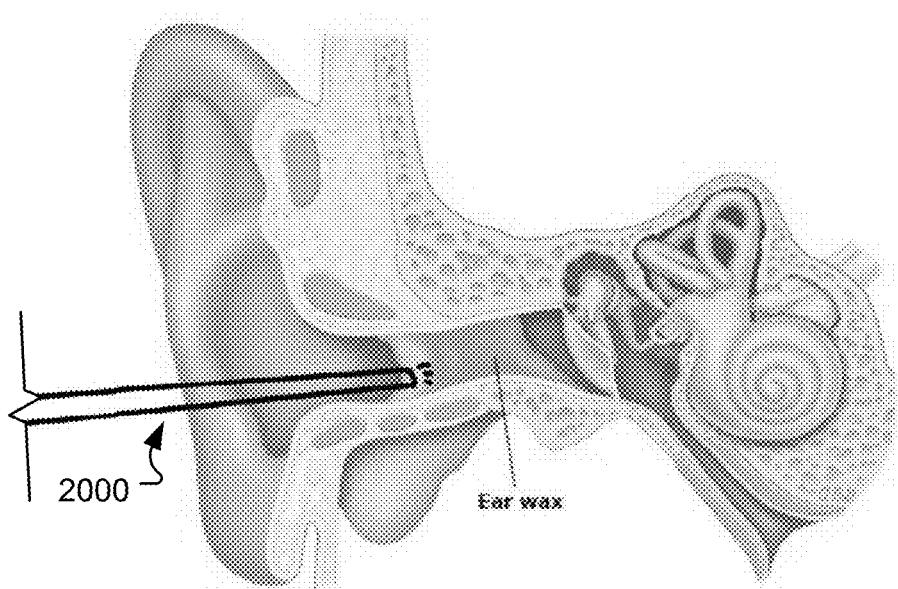
FIGS. 37A and 37B depict the instrument of FIG. 35 in use.
Figure 37B:
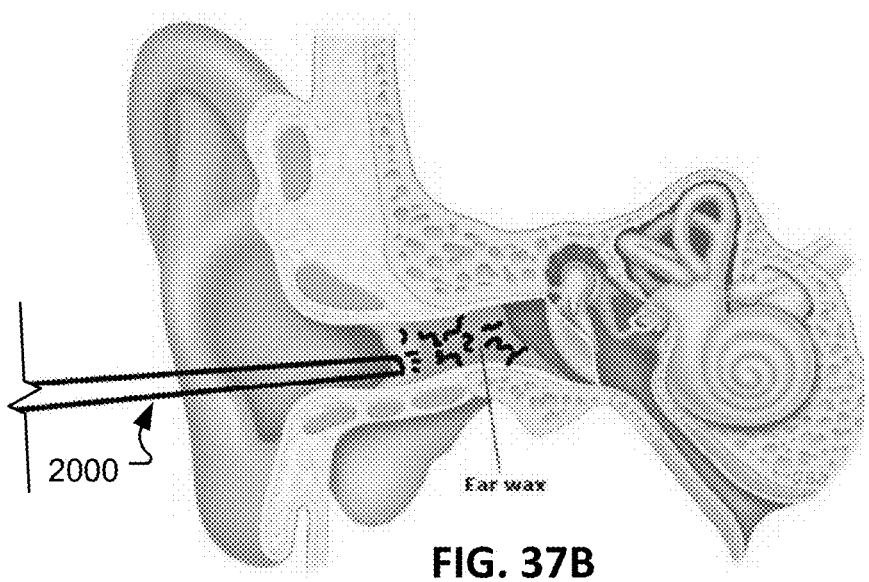

Referring to FIG. 31, in some cases the various otologic procedures described herein can be performed using an example otologic console system 1800. In the current otology surgical suite, there are multiple pieces of equipment each with individual consoles for operation, e.g., a laser, cautery, drills, endoscope, operating microscope, etc. In addition, room suction is used. In many cases, all these pieces of equipment are needed and surgeons and OR staff must move back and forth between consoles throughout the surgical case. Further, there are technologies that could be utilized in otology procedures which are not currently supported in the OR, including micro-diathermy, pneumatic cutters, micro-suction, and ultrasonic cutters/debriders as described above.

The otologic console system 1800 is single station or console that can support multiple modalities would allow for synchronized functionality (e.g., infusion/aspiration, lighting/visualization, laser, etc.) of multiple instruments, and/or control of other treatment devices as described herein (e.g., pneumatic aspirating cutter, laser, ultrasound, diathermy, middle ear flooding, etc.). The otologic console system 1800 broadly includes one or more user displays 1810, one or more user input devices 1820, one or more control such as the depicted foot pedal 1830, and a control system 1840 with one or more processors, computer memory, and other control devices and systems.

In some embodiments, the otologic console system 1800 can include an adjustable room suction controller/limiter. In particular embodiments, the otologic console system 1800 can include an integrated suction pump (e.g., a peristaltic pump) to allow for removal of micro-volumes of fluid with finer control (including, for example, volumetric control), and less trauma than simple room suction.

Room suction is used routinely in otological surgery. A variety of tip diameters are exchanged throughout the case depending on the level of suction required and the anatomical size constraints. Suction tips are generally blunt metal and can cause local trauma. While some suction instruments allow the suction to be controlled on/off with finger actuation, fine control suction force is generally lacking. In the case of cochlear electrode implantation, for example, microliter volumes need to be removed from the delicate round window membrane. The otologic console system 1800, or a stand-alone control unit, could be configured with a peristaltic or venturi pump to allow the clinician 1 to remove fluid with this precision.

A soft, flexible tip on the suction instrument would be advantageous in limiting trauma. The design could also include features that prevent a "seal" against the tissue, limiting the amount of direct suction that could be applied to structures such as the round window membrane or in proximity to the facial nerve. This can be achieved with side slits, holes, or other features which allow air to enter the instrument via a secondary route.

In some embodiments, the suction from or controlled by the console 1800 can be controlled by actuation of the foot pedal 1830 to allow the clinician 1 to augment the amount of suction applied without requiring instrument exchange. Being able to modulate the suction amount from continuous to "on demand" bolus microliter volumes would allow the clinician 1 to fine tune the instrument to the surgical situation, reducing potential trauma.

One or more foot pedals 1830 can provide hands-free control and actuation of the various instruments described herein. In some cases, even small translational movements of instruments resulting from manual actuation can be detrimental in the middle ear space. Further, many mechanical actuation mechanisms require the clinician 1 to move the instrument to accommodate for movement at the tip (e.g., extendable forceps). Combining foot pedal 1830 actuation with otologic instruments which remain stationary at the distal tip during actuation would greatly improve surgical precision.

In addition, the console 1800 can include plug-in support for one or more of: diathermy, laser probe, pneumatic handpieces, infusion, suction/aspiration, ultrasonic handpiece, drill, endoscope and microscope control with foot pedal control.

In some embodiments, the console 1800 is configured to control an infusion line into the middle ear 40 and aspiration of individual instruments to maintain constant fluid volume and pressure. In either case, simultaneous infusion and aspiration would minimize the need for frequent instrument exchanges and allow for more efficient removal of blood and other debris.

FIGS. 32-34B depict an example high-speed rotary aspirating end cutter 1900 that can be incorporated in any of the otologic instruments described herein. The high-speed rotary aspirating end cutter 1900 includes an outer shaft 1910 and an inner rotating shaft 1920. The inner rotating shaft 1920 rotates within the lumen defined by the outer shaft 1910. The end of the outer shaft 1910 defines an opening 1912 that can receive tissue therethrough. In the depicted embodiment, the opening 1912 is a circular segment (e.g., a quarter circle, semi-circle, etc.). Accordingly, as depicted in FIG. 32 tissue can be cut between the outer shaft 1910 and the inner rotating shaft 1920 (e.g., like a "rotary shearing" blade cutter) when the tissue is captured in the opening 1912. When portions of tissue are cut, the tissue portions can be aspirated through high-speed rotary aspirating cutter 1900 as shown.

The high-speed rotary aspirating end cutter 1900 can be useful, for example, for removing middle ear tissue, resurfacing the edges of a tympanic membrane perforation in a tympanoplasty procedure (tympanic membrane repair procedure), and the like. During tympanoplasty, the edges of the existing tympanic membrane perforation are first "freshened" by removing tissue around the perimeter of the perforation. Currently there is no precise instrument for performing this procedure and typically more tissue is removed than necessary, resulting in a larger perforation than necessary, further complicating the subsequent patching procedure. The small rotary end cutter with aspiration provided by the high-speed rotary aspirating end cutter 1900, can ensure more precise cutting of tissues. This can also be combined with liquid infusion or flooding of the middle ear and/or outer ear canal. The high-speed rotary aspirating end cutter 1900 can also have utility in removing membranes and fibrous tissues in the middle ear.

While the tip of the depicted high-speed rotary aspirating end cutter 1900 is blunt, in some embodiments the tip can be beveled, cone-shaped, radiused, and the like.

Removal of material (e.g., tissue, bone, etc.) can be conducted using high-speed rotary aspirating end cutter 1900. Cutting is achieved at the interface of the inner rotating shaft 1920 and the internal wall of the outer shaft 1910 at the location of the opening 1912. The shape and location of the opening 1912 can be configured for optimal contact with the target tissue or material. Since the cutting action occurs just within (approximately the wall thickness of the outer shaft 1910) the external surface of the instrument 1900, the size of the opening 1912 and the aspiration force can be selected to limit damage to the adjacent tissues while maximizing removal of target material. In some embodiments an aspiration channel down the center of the instrument 1900 can assist with pulling the target material into the opening 1912 to facilitate cutting. In some embodiments, the level of aspiration force and cutting speed of the instrument 1900 can be adjusted by a central console (e.g., the console 1800 of FIG. 31) based on the mechanical properties of the target and surrounding tissues. Aspiration would also enable immediate removal of cut or chopped material from the surgical field.

In some cases, such as removing material from bony surfaces of the middle ear, it would be advantageous to have the cutting action located at the end of the instrument ("end cutting"), as provided by the high-speed rotary aspirating end cutter 1900. In such a case, a rotational blade is preferred. In this case, the instrument tip could be blunt, rounded, beveled, or cone shaped, with the cutting blade shape and orientation mirroring the shape and orientation of the opening 1912 to achieve an effective shearing or scissor-like cut.

FIG. 34B depicts an alternative inner rotating shaft 1920a. In this example, the inner rotating shaft 1920a has two end openings. The two end openings provide two tissue cuts per revolution (as compared to the single tissue cut per revolution provided by the inner rotating shaft 1920).

The high-speed rotary aspirating end cutter 1900 is appropriately sized for the application. In the case of earwax removal, in some embodiments the outer diameter of the high-speed rotary aspirating end cutter 1900 would be in the range of 0.4 mm to 4 mm outer diameter, and preferably be less than 2 mm in diameter. The distal shaft portion that is inserted into the ear canal would be 25-70 mm in length, preferably approximately 50 mm in length. The handle would preferably be smaller in diameter in order to not impede visualization of the target area. The handle can be at an angle or curve relative to the distal shaft, or the distal shaft itself can have a curve.

FIGS. 35-37B illustrate another example instrument in accordance with some embodiments. This is an ultrasonic instrument 2000 that can be used for fragmentation or emulsification of ear wax and/or target tissues (e.g., cholesteatoma, pseudomembranes, and bone). The ultrasonic instrument 2000 broadly includes a handle 2010 and a distally-extending shaft 2020. The ultrasonic energy is delivered at least from the distal tip portion of the shaft 2020.

During many otologic procedures, there are materials encountered that are adjacent to tissue or bone that is desirable to maintain or protect, while still wishing to remove the target materials. As examples, cholesteatoma is an abnormal skin growth predominantly in the middle ear that would be ideal for targeted material removal. Pseudomembranes, such as those covering the round window niche, are a commonly occurring growth that would need to be removed to facilitate access to the round window niche and membrane. Highly specific removal of bone is useful for many procedures in the external ear, middle ear, and inner ear.

Earwax, or cerumen, is a material that is produced in the cartilaginous portion of the outer ear and typically is beneficial, but can become deleterious if production is excessive or not balanced by natural removal processes (epithelial migration and jaw motion). Excessive earwax or impacted cerumen can impede the passage of sound, cause mild conductive hearing loss, pain, itchiness, and can even lead to perforated eardrums if the wax is pushed further into the ear. A variety of factors, such as genetics and hearing aid use, can contribute to excessive earwax. Genetics in particular determine whether a given individual has wet or dry earwax.

Earwax removal by otologists, neurotologists or other specialists is typically conducted by curetting, either solely for the patient's benefit or in preparation for other canal-based procedures. While curetting is the dominant method, it is not without risk since the edges of the typically metallic curette are sharp and can easily damage or cause intense pain to the highly sensate ear canal walls.

Earwax removal can be also conducted by primary care clinicians or even as an at-home procedure. Ear swabs are not recommended since these typically push earwax further into the ear and risk eardrum perforation. Typical procedures to remove earwax often include use of softeners (cerumenolytics) as a preparatory step followed by irrigation. Typically cerumenolytics need to be used multiple times a day for 3-5 days before irrigation, which can be a burdensome step which presents challenges for compliance. These earwax removal procedures are surprisingly common, as many as 150,000 ears are irrigated each week in the US. Unfortunately irrigation is often poorly executed and complications such as infection (otitis), dizziness, pain, vertigo, tinnitus, and particularly damage or perforation of the eardrum can occur. Major complications occur in 1 in 1,000 ears.

The ultrasonic instrument 2000 advantageously provides a method and device for earwax removal that can selectively remove earwax without damaging the canal walls or eardrum. The ultrasonic instrument 2000 is easy to use and is additionally advantageous because it can expand the site of care (e.g., moving a method from a specialists' office to primary care, or from primary care to home use).

The use of ultrasonic emulsification (e.g., as provided by the ultrasonic instrument 2000) or the use of cutting (e.g., as provided by the high-speed rotary aspirating end cutter 1900 described above) can be highly advantageous for the removal of earwax, among other uses. The energy frequency, tip geometry, or other properties of the ultrasonic instrument 2000 can be tuned to be selective for material, such as earwax, while still limiting damage to adjacent tissue or skin such as the ear canal skin. The ultrasonic instrument 2000 can degrade or emulsify the target material. If the ultrasonic instrument 2000 has built in aspiration, it can aspirate at the same time as emulsifying the earwax which effectively removes the earwax in a precise and easy to visualize manner. The precision and easy visualization are other ways to enable limiting damage to adjacent tissue. The use of such an ultrasonic emulsifier to remove earwax would therefore be in many ways superior to existing earwax removal for otologists, while also being accessible and usable by primary clinicians in such a way that could decrease the common complications associated with extant methods.

Ultrasonic instruments are frequently used with a liquid medium surrounding the target tissue to conduct the ultrasonic energy. In otology, however, the procedures are typically performed without submerging or liquid encapsulating the target area, and the surgical spaces encountered are typically air-filled. The middle ear, as an example, is one of the rare cavities in the body that is air-filled rather than fluid-filled. As such, it can be envisioned that ultrasonic cutting or emulsification is challenging without requiring either much higher energy delivery, which might quickly damage instrumentation due to excessive generation of heat. It has been observed that using existing ultrasonic cutters or fragmatomes in air at room temperature rapidly results in instrument failure and fracture.

It can be envisioned that for use in air-filled cavities or spaces that are easily accessible and able to be filled with liquid media (such as filling the external ear canal with saline), that such a method of filling the space with liquid media would be beneficial for enabling the use of instruments that are typically problematic to use in air.

The ultrasonic instrument 2000 addresses the use of an ultrasonic cutters/debrider in air. In some embodiments, the ultrasonic instrument 2000 has an additional cooling mechanism internal to the distal shaft 2020. Referring to the various example transverse cross-sectional views shown in FIGS. 36A-E, in some embodiments the shaft 2020 defines one or more channels that can convey liquids as an internal cooling mechanism. For example, the shaft 2020 can define an out-going channel (towards distal tip portion) and an in-flowing channel (toward proximal handle 2010) that permit fluid flow in order to transfer heat away from the distal tip of the shaft 2020.

It can be envisioned that the in-flowing and out-going channels (which are conjoined) could extend along the shaft 2020 in a variety of configurations such as straight (linear), helical, oscillating (zig-zag) or other paths/shapes that permit fluid and air flow and associated movement of thermal energy. The channel(s) can be cut from or embedded in the shaft 2020 of the device 2000, or be free-floating within the shaft 2020 and made of either metallic (such as stainless steel, titanium, or other metals) or polymeric (such as silicone, polyurethane, PDMS, nylon, or other) material. The channels can be predominantly in the center of the shaft 2020, or predominantly in the exterior region of the shaft 2020 (as shown in FIG. 36B). The channels can have cross sections that are circular (e.g., FIGS. 36A, 36D, and 36E), arcuate annular (e.g., FIG. 36B), hemispherical, semicircular (e.g., FIG. 36C) or other shapes. Channels predominantly on the outside portion of the shaft 2020 can be advantageous for permitting increased contact area as well as protecting the patient from heat developed by internal elements.

The fluid used for liquid cooling (e.g., heat transfer fluid) can be water, saline, deionized water, glycol/water solutions (ethylene glycol or propylene glycol), ethanol, alcohols, high viscosity oils, dielectric fluids such as fluorocarbons and PAO, silicone oils, viscoelastics (e.g., sodium hyaluronate-based), or other fluids that are suitable for heat transfer. The fluid can even be a pressurized gaseous media that would typically be gas at ambient pressure. Preference will be given to fluids that have better biocompatibility (such as water-based) to mitigate the risks associated with device breakage as well to facilitate manufacture, sterilization, and packaging of the device. Ideally heat transfer fluids have high thermal conductivity. Cavitation and convection associated with ultrasonic delivery of the energy can result in additional cooling. The fluid can be supplied to the ultrasonic instrument 2000 while chilled below room temperature, or at room temperature.

It can be envisioned that, in some embodiments, there can be a single out-going (towards the distal tip) fluid flow, such as with irrigation. This would permit cooling of the shaft 2020 while also supplying a limited amount of liquid in the target region at the distal tip, which would add the advantage of serving as a conduction medium and increasing the efficacy of the energy delivery/lowering the energy required to degrade or emulsify the target material.

It can also be envisioned that a single suction or aspiration throughway/channel would serve as another heat transport mechanism to aid in cooling. Accordingly, for either the outgoing or incoming channels, they can be of a variety of configurations (such as described above) to aid in increasing contact area or heat transfer efficiency.

It can be envisioned that having both irrigation and aspiration channels within the shaft 2020 would capture the benefits of each, while simultaneously acting effectively as cooling to the ultrasonic instrument 2000. Irrigation and aspiration through the ultrasonic instrument 200 could be controlled by a central console (such as the console 1800 described in reference to FIG. 31) in order to maintain a constant fluid volume in which to perform the procedure. Temperature within the ultrasonic instrument 2000 could be monitored by the console 1800, which could trigger increases in irrigation and/or aspiration rates as needed to maintain cooling.

FIGS. 36A-E show cross-sections of various types of shafts 2020. Each has a first channel 2022a and a second channel 2022b. In some embodiments, the shaft 2020 only has a single channel 2022a or 2022b. The channels 2022a-b can be used for transmitting cooling fluid or for aspiration and/or irrigation. FIG. 36A depicts an embodiment of the shaft 2020 that is solid except for the channels 2022a-b that have circular cross-sections. FIG. 36B depicts an embodiment of the shaft 2020 that is solid except for the channels 2022a-b that have arcuate annular cross-sections. FIG. 36C depicts an embodiment of the shaft 2020 that is hollow and defines channels 2022a-b that have semicircular cross-sections. FIG. 36D depicts an embodiment of the shaft 2020 that is hollow and contains two parallel tubular channels 2022a-b that have circular cross-sections. FIG. 36E depicts an embodiment of the shaft 2020 that is hollow and defines/contains two concentric channels 2022a-b that have circular cross-sections (although channel 2022a is actually a cross-section of a torus/toroid or donut-shape).

In another embodiment, the ultrasonic instrument 2000 has one or more heat sinks (e.g., with fins) along the shaft 2020 defining channels for air to circulate outward (towards distal tip) and an inward (toward proximal handle). Such a configuration can utilize conduction and convection, as applicable, to transfer heat.

It can be envisioned that there are other methods or mechanisms for localized cooling of the shaft 2020, such as thermoelectric cooling, that would be advantageous either due to efficacy, size, efficiency, or cost to manufacture. Thermoelectric cooling utilizes the application of electric current to generate heat exchange between heat source and a heat sink, and as such functions as a solid-state heat pump. It can be envisioned that the heat sink could be placed in the handle 2010 of the ultrasonic instrument 2000 or more proximally to allow transfer heat away from heat sources at the distal tip and shaft 2020. Thermoelectric cooling has the additional advantage of not requiring moving parts which potentially enhances device reliability and manufacturing ease, while also removing the concern over having a heat transfer media that could leak.

As another approach to enabling use of the ultrasonic instrument 2000 in an air environment, piezoelectric elements that are suitable for higher temperatures can be used. There are many ferrolectric/piezoelectric materials available such as lead zirconate-titanate PZT, modified PZT, bismuth titanate Bi4Ti3O12, modified bismuth titanate, lithium niobate LiNbO3, LNN based on LiNbO3, lead metaniobate PbNb2O6, modified lead titanate, modified lead metaniobate, galium orthophospate GaPO4, aluminum nitride AlN, BMT-PT, BS-PT, sol-gel sprayed films, as well as others that could be considered for such a use.

In all of the above instrument embodiments, any of the functional end effectors, handle angulations, shaft curves or angulations, markings, actuation mechanisms, steerability mechanisms, deflectability mechanisms, irrigation and/or aspiration channels, and any other features described above may be combined in any variety of permutations and embodiments.

The devices, systems, materials, compounds, compositions, articles, and methods described herein may be understood by reference to the above detailed description of specific aspects of the disclosed subject matter. It is to be understood, however, that the aspects described above are not limited to specific devices, systems, methods, or specific agents, as such may vary. It is also to be understood that the terminology used herein is for the purpose of describing particular aspects only and is not intended to be limiting.

While the instruments disclosed herein are primarily described in the context of otologic procedures that are either in the outer ear or that use a trans-canal trans-tympanic membrane approach to the middle ear, it should be understood that the instruments are not limited to such uses. For example, in some embodiments the instruments described herein can be used in combination with other access methods and techniques including, but not limited to, trans-mastoid access, trans-canal access via tympanomeatal flap, endaural, retroaural, postaural, nasopharyngeal, any of the previously described approaches to achieve eustachian tube access, and others.

A number of embodiments have been described. Nevertheless, it will be understood that various modifications may be made without departing from the claim scope herein. Accordingly, other embodiments are within the scope of the following claims.

What is claimed is:

1. A method of treating a middle ear or inner ear disorder of a patient, the method comprising:
   implanting a port device in an annulus tympanicus, and
   accessing the middle ear of the patient by advancing a distal end portion of an otologic instrument through or adjacent to the annulus tympanicus of the patient, wherein the advancing the distal end portion of the otologic instrument through or adjacent to the annulus tympanicus is performed by passing the distal end portion of the otologic instrument through a passage defined by the port device.

2. The method of claim 1, wherein the passage is curved and causes the distal end portion of the otologic instrument to curve as the distal end portion of the otologic instrument is passed through the passage.

3. The method of claim 1, wherein the otologic instrument is a first otologic instrument, and further comprising accessing the middle ear of the patient by advancing a distal end portion of a second otologic instrument through or adjacent to the annulus tympanicus of the patient.

4. The method of claim 3, wherein the distal end portions of the first and second otologic instruments are in the middle ear concurrently.

5. The method of claim 4, wherein the first otologic instrument is an endoscope and the second otologic instrument is a diathermy instrument or an ultrasonic instrument.

6. The method of claim 4, wherein the first otologic instrument is an endoscope and the second otologic instrument is an aspirating tissue cutter instrument.

7. The method of claim 1, further comprising:
   flooding the middle ear with a liquid; and
   while the middle ear is flooded with the liquid, treating the middle ear or inner ear disorder using the otologic instrument.

8. The method of claim 4, further comprising:
   while both the first and second otologic instruments are positioned through or adjacent to the annulus tympanicus, concurrently using the first otologic instrument to provide direct visualization within the middle ear and using an end effector of the second otologic instrument within the middle ear to grasp tissue, cut tissue, cauterize tissue, inject a therapeutic formulation, aspirate fluid, irrigate fluid, or a combination thereof.

9. A method of treating a middle ear or inner ear disorder of a patient, the method comprising:
   making a puncture or incision in or adjacent to an annulus tympanicus;
   accessing the middle ear of the patient by advancing a distal end portion of an otologic instrument through or adjacent to the annulus tympanicus of the patient, wherein the advancing the distal end portion of the otologic instrument through or adjacent to the annulus tympanicus is performed by passing the distal end portion of the otologic instrument through the puncture or incision, wherein the otologic instrument is a first otologic instrument; and
   accessing the middle ear of the patient by advancing a distal end portion of a second otologic instrument through or adjacent to the annulus tympanicus of the patient, wherein the distal end portions of the first and second otologic instruments are in the middle ear concurrently,
   wherein the first otologic instrument is an endoscope and the second otologic instrument is an injection instrument configured to deliver a therapeutic formulation within the middle ear.

10. The method of claim 9, wherein the injection instrument is configured to deliver a therapeutic formulation to a round window niche within the middle ear and comprises: a handle defining a longitudinal handle axis; an actuation mechanism coupled to the handle; and an injection instrument shaft extending distally from the handle along a longitudinal shaft axis, wherein a non-zero angle is defined between the longitudinal shaft axis and the longitudinal handle axis.

11. The method of claim 10, wherein a ratio of a length of the injection instrument shaft to a diameter of the distal end portion of the injection instrument shaft is 400:1 to 50:1.

12. The method of claim 11, wherein the diameter of the distal end portion of the injection instrument shaft is 0.1 mm to 0.7 mm.

13. The method of claim 12, wherein the length of the injection instrument shaft is 30 mm to 90 mm.

14. The method of claim 13, wherein the non-zero angle defined between the longitudinal shaft axis and the longitudinal handle axis of the injection instrument is 10° to 70°.

15. The method of claim 9, wherein the endoscope is configured to provide direct visualization of the injection instrument within the middle ear and comprises: a handle defining a longitudinal handle axis; an actuation mechanism coupled to the handle; and an injection instrument shaft extending distally from the handle along a longitudinal shaft axis, wherein a non-zero angle is defined between the longitudinal shaft axis and the longitudinal handle axis.

16. The method of claim 13, wherein the non-zero angle defined between the longitudinal shaft axis and the longitudinal handle axis of the endoscope is 10° to 70°.

17. A method of treating a middle ear or inner ear disorder of a patient, the method comprising:

making a puncture or incision in or adjacent to an annulus tympanicus;

accessing the middle ear of the patient by advancing a distal end portion of an otologic instrument through or adjacent to the annulus tympanicus of the patient, wherein the advancing the distal end portion of the otologic instrument through or adjacent to the annulus tympanicus is performed by passing the distal end portion of the otologic instrument through the puncture or incision, wherein the otologic instrument is a first otologic instrument;

accessing the middle ear of the patient by advancing a distal end portion of a second otologic instrument through or adjacent to the annulus tympanicus of the patient, wherein the distal end portions of the first and second otologic instruments are in the middle ear concurrently; and while both the first and second otologic instruments are positioned through or adjacent to the annulus tympanicus, concurrently using the first otologic instrument to provide direct visualization within the middle ear and using an end effector of the second otologic instrument within the middle ear to grasp tissue, cut tissue, cauterize tissue, inject a therapeutic formulation, aspirate fluid, irrigate fluid, or a combination thereof, wherein the first otologic instrument is an endoscope and the second otologic instrument is an injection instrument configured to deliver the therapeutic formulation to a round window niche within the middle ear.

* * * * *